(12) United States Patent
Zhao et al.

(10) Patent No.: US 7,838,501 B2
(45) Date of Patent: Nov. 23, 2010

(54) COUMERMYCIN/NOVOBIOCIN-REGULATED GENE EXPRESSION SYSTEM

(75) Inventors: Hui-Fen Zhao, LaSalle (CA); Shi-Hsiang Shen, Beaconsfield (CA)

(73) Assignee: National Research Council of Canada, Ottawa, ON (CA)

( * ) Notice: Subject to any disclaimer, the term of this patent is extended or adjusted under 35 U.S.C. 154(b) by 0 days.

(21) Appl. No.: 10/559,411

(22) PCT Filed: Jun. 9, 2004

(86) PCT No.: PCT/CA2004/000854

§ 371 (c)(1),
(2), (4) Date: Aug. 11, 2006

(87) PCT Pub. No.: WO2004/108933

PCT Pub. Date: Dec. 16, 2004

(65) Prior Publication Data

US 2007/0026486 A1 Feb. 1, 2007

Related U.S. Application Data

(60) Provisional application No. 60/477,055, filed on Jun. 10, 2003.

(51) Int. Cl.
*A01N 43/04* (2006.01)
*C12N 5/00* (2006.01)
*A61K 48/00* (2006.01)

(52) U.S. Cl. .................. 514/44 R; 435/320.1; 424/93.2

(58) Field of Classification Search .................. 514/44; 435/320.1; 424/93.2
See application file for complete search history.

(56) References Cited

U.S. PATENT DOCUMENTS 6,187,757 B1 * 2/2001 Clackson et al. .............. 514/31
2003/0166191 A1 * 9/2003 Gardner et al. .............. 435/184

OTHER PUBLICATIONS

Pollock et al. Nature Biotech. 20:729-733; 2002.*
Mohi et al. Mol: Biol. Cell 9:3299-3308; 1998.*
Mohi, M. et al. Mol. Biol. Cell 9:3299-3308; 1998.*
Park, S. et al. Methods 28:346-352; 2002.*
Weiss et al. Biochem. 26:897-904; 1987.*
Hu et al. Structure 3:431-433; 1995.*
NCBI GenBank Accession No. BAA01369; submitted Feb. 17, 1992; pp. 1-3.*
Rittner et al. J. Mol. Biol. 248: 562-580; 1995.*
Saez, E., No, D., West, A., and Evens, R.M. (1997) Curr. Opin. Biotehcnol. 8, 608-616.
Harvey, D., and Caskey, C. (1998) Curr. Opin Chem. 2, 512-518.
Gingrich, J. and Roder, J. (1998) Annu. Rev. Neurosci. 21, 377-405.
DeMayo, F.J., and Tsai, S.Y. (2001) Trends Endocrinol. Metab. 12, 348-353.
Urlinger, S., Baron, U., Thellmann, M., Hasan, M.T., Bujard, H., and Hillen, W. (2000) Proc. Natl. Acad. Sci U.S.A. 97, 7963-7968.
Riond, J.L., and Riviera, J.E. (1988) Vet. Human Toxicol. 5,431-443.
Farrar, M.A., Olson. S.H., and Perimutter, R.M. (2000) Methods Enzymol 327, 421-429.
Pabo, C.O., Sauer, T.T., Sturtevant, J.M., and Ptashne, M. (1979) Proc. Natl. Acad. Sci. U.S.A. 76, 1608-1612.
Weiss. M.A., Paco, C.O., Karplus, M., and Sauer. R.T. (1987) Biochemistry 26, 897-904.
Gossen, M., and Bujard, H. (1992) Proc. Natl. Acad. Sci U.S.A. 89, 5547-5551.
Kim, Y.I., and Hu, J.C. (1995) Proc. Natl. Acad. Sci. U.S.A. 92, 7510-7514.
Byrne, B.J., Davis, M.S., Yamaguchi, J., Bergsama, D.J., and Subramanian, K.N. (1983) Proc. Natl. Acad. Sci U.S.A. 80, 721-725.
Pastorino, J.G., Chen, S.-t., Tafani, M., Snyder, J.W., and Farber J.L. (1998) J. Biol. Chem. 273, 7770-7775.
Gu, J., Shang, L., Huang, X., Lin, T.Yin, M., Xu, K., Ji, L., Roth, J.A., and Fang. B. (2002) Oncogene 21, 4757-4764.
Kobayashi, T., Sawa, H., Morikawa, J., Ueno, S., Katayama, N., Zhang, W., and Shiku, H. (2002) Int. J. Oncol. 20, 723-728.
O'Farrell, A.M., Liu, Y., Moore, K.W., and Mui, A.L. (1998) EMBO J. 17, 1006-1018.
Gormley, N. A., Orphanides. G., Meyer, A., Cullis, P.M., and Maxwell, A. (1996) Biochemistry 35, 5083-5092.
Godfrey, J.C., and Price, K.E. (1972) Adv. Appl. Microbiol. 15, 231-296.
Eder, J.P., Wheeler, C.A. Teicher, B.A. and Schipper, L.E. (1991) Cancer Res. 52, 510-513.
Chrast-Balz, J., and Van Huijsduijnen, R.M. (1996) Nucleic Acids Res. 24, 2900-2904.
Amara, J.F., et al, Proceedings of the National Academy of Sciences of the United States of America, 1997, vol. 94 p. 10618-10623.
Pollock R. and Clackson T., Current Opinion in Biotechnology, 2002, vol. 13, p. 459-467.
Ali, J.A. et al, Biochemistry, 1993, vol. 32, p. 2717-2724.
Japanese Examiner's Report relating to corresponding Japanese Application No. 2006-515586, dated Mar. 17, 2010; including unofficial English translation thereof.
Adachi, I. et al, Nucleic Acids Research, 1987, vol. 15, No. 2, pp. 771-784.

* cited by examiner

*Primary Examiner*—Fereydoun G Sajjadi
(74) *Attorney, Agent, or Firm*—Johanna Coutts; Cassan MacLean

(57) ABSTRACT

A chimeric transactivator comprises a transcription activation domain, a repressor protein DNA binding domain and the bacterial DNA gyrase B subunit. A target gene is operatively linked to operator DNA sequences recognized by the repressor binding domain. The addition of the antibiotic coumermycin results in a coumermycin-switched dimerization of the transactivator, which then binds to operator DNA sequences and activates transcription of the target gene. The addition of novobiocin switches off expression of the target gene by abolishing coumermycin-induced dimerization of the transactivator.

26 Claims, 6 Drawing Sheets

A

B

A

B

COUMERMYCIN/NOVOBIOCIN-REGULATED GENE EXPRESSION SYSTEM

This is a national phase entry application claiming the benefit of PCT Application No. PCT/CA2004/000854, which claims priority to U.S. Provisional Patent Application No. 60/477,055 filed Jun. 10, 2003.

FIELD OF THE INVENTION

This invention relates to the regulation of gene expression.

BACKGROUND OF THE INVENTION

Genetic manipulation of gene expression in mammals holds great potential for functional studies of particular genes and their products, and in applications for drug discovery and gene therapy. An ideal gene regulation system would be low in basal activity, but highly and specifically responsive to the induction. In addition, the expression of a given gene should be dose-responsive, and the system could be reversibly switched on or off promptly. This is particularly valuable for gene therapy in which pharmacological control over timing and levels of a particular gene expression within a therapeutic range is critical for certain diseases.

Recently, several inducible systems for mammalian cells have been developed. These with their variants include FK506/rapamycin, RU488/mifepristone, ecdysone-inducible, and tetracycline (Tet) inducible systems (1-4). Currently, the Tet-inducible system is most commonly used for regulated gene expression in vivo. Significant improvements have been made in this Tet system to reduce its basal expression level and to improve its inducibility in vivo (5). However, one major shortcoming for this system is the lack of an effective antagonist for its inducers; the potent inducer doxycycline, for example, has a considerable half-life (about 24 hr) in vivo (6). This pharmacokinetic property may exclude its use in situations where prompt and efficient on/off switching is essential, such as for gene therapy or for precise regulated expression of specific genes during development (1).

SUMMARY OF THE INVENTION

The present invention provides recombinant nucleic acid molecules encoding a chimeric transactivator comprising a transcription activation domain, a repressor protein DNA binding domain, and the bacterial DNA gyrase B subunit (GyrB). The transactivator is designed to activate transcription of a target gene, where the target gene is operatively linked to operator DNA sequences recognized by the repressor protein DNA binding domain. The transactivator has a low basal activity, meaning that very little transcription of the target gene occurs unless the transactivator is enabled.

When an effective amount of coumermycin is added, coumermycin-switched dimerization of the GyrB allows the transactivator to bind to the operator DNA sequences, thus activating transcription of the target gene. The transactivator is disabled when an effective amount of novobiocin is added; novobiocin abolishes the coumermycin-induced dimerization of the transactivator, thus switching off expression of the target gene.

The system is effective for tightly regulating gene expression in stable mammalian cell lines, and is therefore useful for applications requiring rapid on/off switching of gene expression, including gene therapy.

Accordingly, the present invention provides a nucleic acid molecule encoding a biologically active chimeric transactivator protein that comprises a functional DNA binding domain of a repressor protein, wherein the binding domain is not capable of dimerization; bacterial DNA gyrase B subunit (Gyr B); and a transcription activation domain.

The present invention flier provides an expression vector comprising a nucleic acid molecule operatively linked to an expression control sequence, the nucleic acid molecule encoding a biologically active chimeric transactivator protein that comprises a functional DNA binding domain of a repressor protein, wherein the binding domain is not capable of dimerization; bacterial DNA gyrase B subunit (Gyr B); and a transcription activation domain.

The present invention further provides a host cell comprising an expression vector comprising a nucleic acid molecule operatively linked to an expression control sequence, the nucleic acid molecule encoding a biologically active chimeric transactivator protein that comprises a functional DNA binding domain of a repressor protein, wherein the binding domain is not capable of dimerization; bacterial DNA gyrase B subunit (Gyr B); and a transcription activation domain.

The present invention further provides a kit comprising an expression vector comprising a nucleic acid molecule encoding a biologically active chimeric transactivator protein that comprises a functional DNA binding domain of a repressor protein, wherein the binding domain is not capable of dimerization; bacterial DNA gyrase B subunit (Gyr B); and a transcription activation domain, in a pharmaceutically suitable carrier, wherein the expression vector is administered externally, perorally, intravesicularly, nasally, introbronchially or into the gastrointestinal tract, or which is injected into an organ, into a body cavity, into the muscle system, subcutaneously or into the blood circulation, for the prophylaxis or therapy of a disease.

The present invention further provides a method for regulating the expression of a target gene in a host cell, comprising the steps of introducing into the host cell an expression vector comprising a nucleic acid molecule operatively linked to an expression control sequence, the nucleic acid molecule encoding a biologically active chimeric transactivator protein that comprises a functional DNA binding domain of a repressor protein, wherein the binding domain is not capable of dimerization; bacterial DNA gyrase B subunit (Gyr B); and a transcription activation domain; allowing expression of the biologically active chimeric transactivator encoded by said expression vector; introducing an effective amount of coumermycin or a derivative thereof into said cell to increase expression of said target gene; and introducing an effective amount of novobiocin or a derivative thereof into said cell to decrease expression of said target gene.

The present invention further provides a method for regulating expression of a therapeutic gene product to a patient in need of said therapeutic gene product, comprising introducing into a patient an expression vector comprising a nucleic acid molecule operatively linked to an expression control sequence, the nucleic acid molecule encoding a biologically active chimeric transactivator protein that comprises a functional DNA binding domain of a repressor protein, wherein the binding domain is not capable of dimerization; bacterial DNA gyrase B subunit (Gyr B); and a transcription activation domain; treating the patient with an effective amount of coumermycin or a derivative thereof, said coumermycin binding to said transactivator, thereby activating expression of the gene encoding said therapeutic gene product; and treating the patient with an effective amount of novobiocin or a derivative thereof, said novobiocin binding to said transactivator, thereby preventing transcription and deactivating expression of the gene encoding said therapeutic gene product.

DETAILED DESCRIPTION OF THE INVENTION

To fulfill the requirement of precise and efficient on/off interchange for regulated gene expression, we have explored the use of coumarin antibiotics as inducer and counter-inducer. Coumermycin is a natural *Streptomyces* product consisting of two identically substituted coumarin rings joined by a methyl pyrrole linker (7). A related antibiotic, novobiocin, can be considered as the monomer of coumermycin. Both coumermycin and novobiocin bind to the amino-terminal subdomain (24K) of the bacterial DNA gyrase B subunit (GyrB) (SEQ ID NOS. 1 and 2) resulting in inhibition of bacterial growth (8). Coumermycin binds GyrB with a stoichiometry of 1:2, while its monomeric novobiocin binds GyrB as 1:1 ratio; hence, coumermycin acts as a natural dimerizer of GyrB while novobiocin acts as an antagonist for coumermycin by dissociating dimerized GyrB (9). Derivatives of coumermycin having the ability to bind to and dimerize GyrB, and derivatives of novobiocin having the ability to bind to GyrB and prevent its dimerization, would also be suitable for this system.

To make coumermycin an effective inducer, the DNA binding domain of a repressor protein may be used. The repressor protein should retain its ability to bind operable DNA when its dimerization domain has been deleted. One suitable repressor protein is the λ repressor (λR) (SEQ ID NOS. 5 and 6), the cI gene product of bacteriophage λ, as only its homodimer can bind to λ operator (λOP) DNA (10). λR is composed of an N-terminal domain (residues 1-92) and a C-terminal domain (residues 132-236)(11). The binding of the two N-terminal domains to operator DNA is mainly driven by the C-terminal domain-mediated homodimerization of the repressor though the N-terminal domain itself retains a weak dimerization activity (12). Thus, we have constructed a coumarin-modulated chimeric transactivator by fusing the N-terminal domain of λR to GyrB followed by a transcription activation domain at the C-terminus. Suitable transcription activation domains include those from transcription factors NFκB p65, VP16, B42, and Gal4. Here we describe the development of such a coumermycin/novobiocin-regulated gene expression system and demonstrate that in combination with directed mutagenesis of λR for reduction of basal activity, the expression of genes in vivo is effectively and reversibly regulated by coumarin antibiotics through dimerization of the chimeric λR-GyrB transactivator. This new inducible gene expression system should facilitate functional genome research and broaden the utility of regulated gene expression, particularly for gene therapy and other applications requiring rapid and thorough on/off switching.

Figure 4:
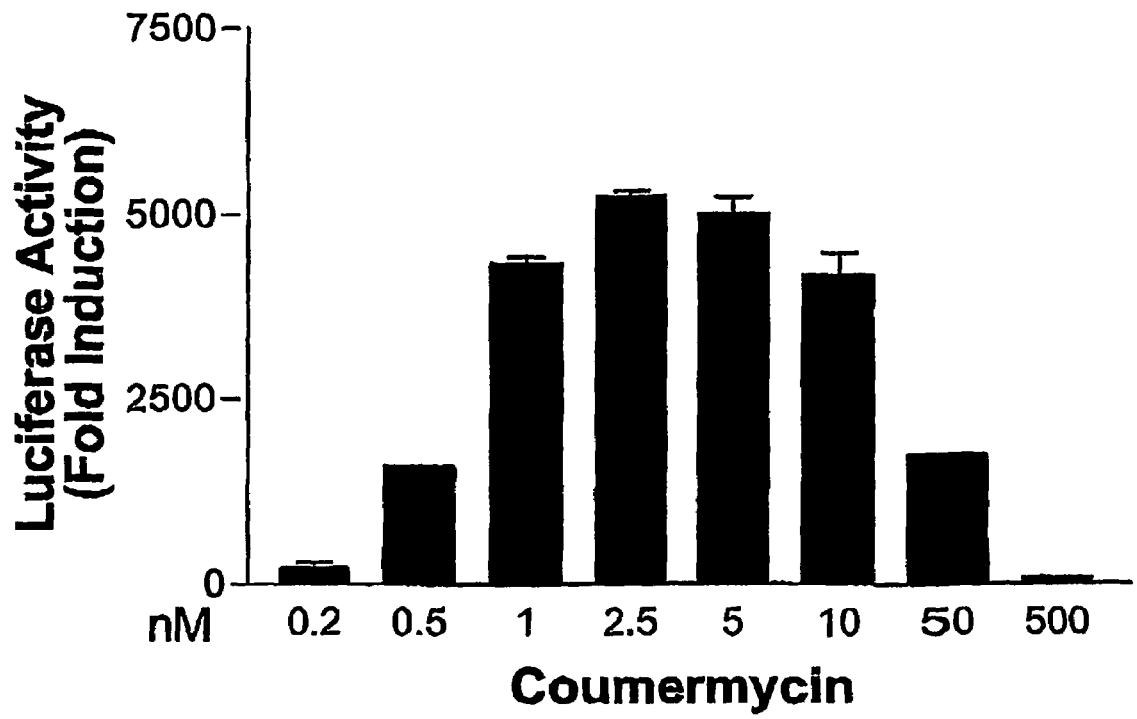
FIG. 4A shows results of an assay testing activation of the luciferase gene at various concentrations of coumermycin.
FIG. 4B shows results of an assay testing activation of the luciferase gene by coumermycin over a period of 72 hours.
Figure 4:
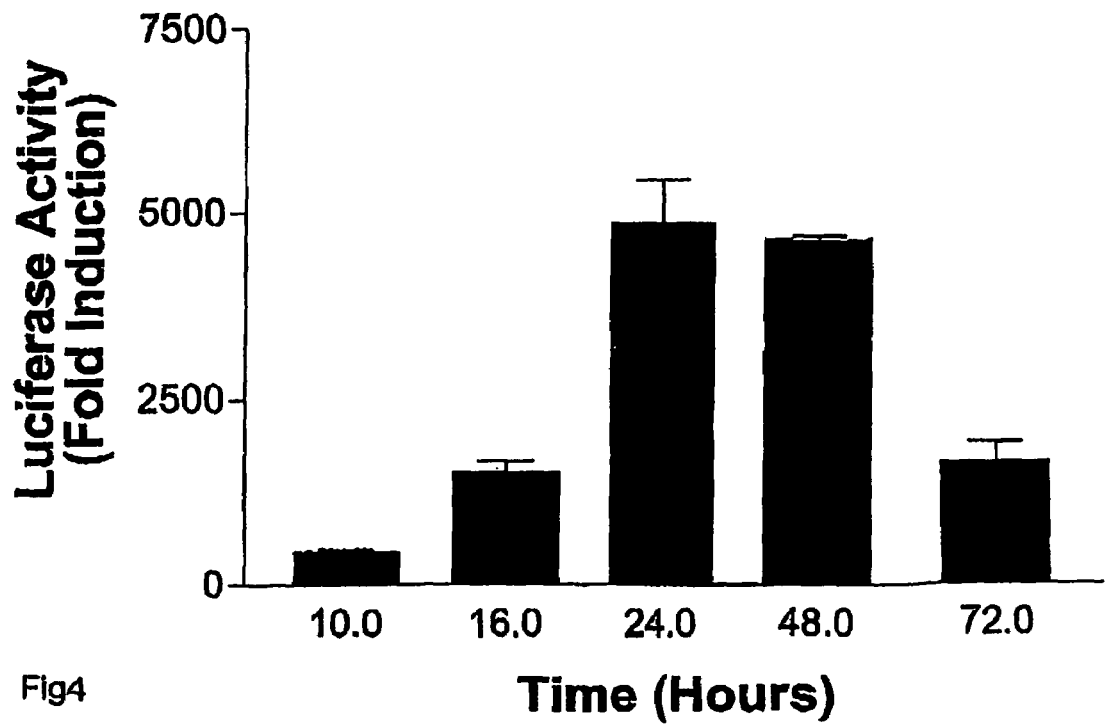

Coumermycin-induced dimerization of GyrB-fusion proteins has recently been explored for characterization of a number of signal transduction pathways (7,19). As with these reports, employing coumermycin/novobiocin to switch dimerization of chimeric λR-GyrB transactivator possesses several favorable characteristics, and offers particular advantages for in vivo gene expression. First, both coumermycin and novobiocin bind GyrB with high affinity (Kd $3-5\times10^{-8}$M) (20), resulting in potent activity of these coumarins at very low concentrations for induction and anti-induction of GyrB dimerization. Indeed, we found that coumermycin was able to induce appreciable gene expression via dimerization of the λR-GyrB transactivator at a concentration as low as 0.5 nM. Second, the specificity of these coumarin antibiotics for the prokaryotic enzyme is well established; no endogenous binding targets with high affinity are known to exist in mammalian cells. This makes coumermycin a very favorable inducer for regulated gene expression in mammalian cells. Thirdly, both coumermycin and novobiocin display excellent pharmacokinetic properties in vivo as the reported serum half-life for coumermycin is 5.5 hr (21) and for novobiocin is 6 hr (22). In addition, novobiocin is clinically approved for antibiotic use. For coumermycin, extensive animal testing at concentrations effectively exerting antibacterial activity has also revealed no overt toxicity. In the current system, we demonstrate that coumermycin can effectively induce gene expression at concentrations between 0.5 nM and 50 nM, a fairly broad dose range for administration of the drug in vivo. The concentration of coumermycin in this dose range for induction is far below 20 μM, a dose causing cellular toxicity in vivo. However, higher doses of coumermycin (>0.5 μM) have caused a reduced induction of gene expression in this system (FIG. 4A). This is due to the fact that at high concentration of coumermycin the excess drug will lead to dissociation of GyrB dimer.

Figure 5:
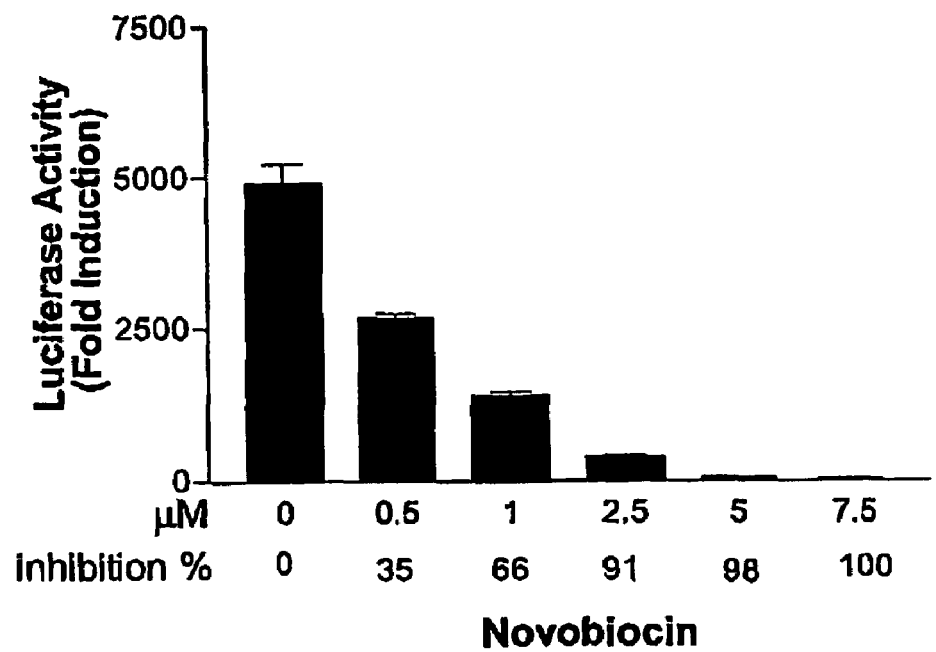
FIG. 5A shows results of an assay testing activation of the luciferase gene at various concentrations of novobiocin.
FIG. 5B shows results of an assay testing activation of the luciferase gene in the presence of coumermycin alone and in the presence of both coumermycin and novobiocin, over a 50 hour period.
Figure 5:
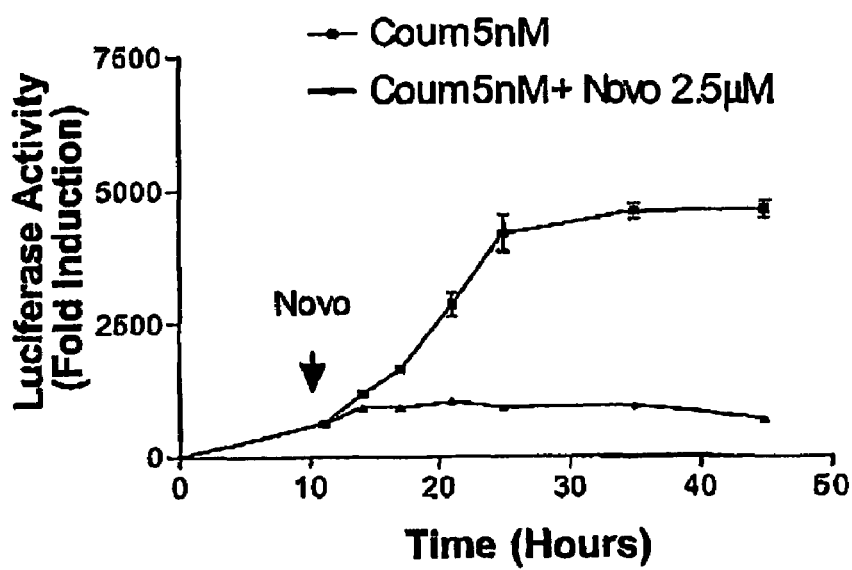

In comparison with the Tet-inducible system, one advantage offered by the λR-GyrB system is its very rapid on-off switching for controlled gene expression. Two unique features in this system contribute to this valuable function. First, both coumermycin and novobiocin, as mentioned before, have a very short in vivo half-life (6 hr) that is about one-third of Tet-inducer doxycycline (12-24 hr) (23). More importantly, in this λR-GyrB system, novobiocin, the monomeric form of coumermycin, can be used as an anti-inducer to block coumermycin-induced gene expression, thus making novobiocin a valuable antagonist to coumermycin for prompt shut-down of the drug-induced gene expression as demonstrated in this study (FIG. 5B). Although the binding affinity of novobiocin to GyrB is comparable to that of coumermycin, the concentration of novobiocin required to completely block the coumermycin-induced gene expression is approximately a thousand-fold that of the inducer. This is consistent with the previous report for dissociation of Raf-GyrB dimer (24). One explanation for this is that while nanomolar concentration of coumermycin (1 nM) would dimerize enough GyrB molecules (about 2 nM) to bind operator sites for activation, novobiocin has to saturate all GyrB molecules existing in the cells to prevent their dimerization for dissociation of the dimerized GyrB molecules through competition with coumermycin. The total concentration of GyrB molecules accumulated in the cells could greatly exceed the dimerized GyrB molecules in this inducible system.

The inducibility of this λR-GyrB-based system, as with other regulated gene expression systems, is dependent on the activation potency of the transactivator and on the magnitude of basal expression, the latter of which is contributed primarily by the intrinsic dimerization capability of λR-GyrB in the absence of coumermycin. As reported previously (12), the N-terminal domain of wild type a retain an appreciable capacity for intrinsic dimerization through the helix5-helix5 interaction, which in this system led to a high basal expression level. We therefore performed a random mutagenesis on the related residues in this domain, and found that a number of mutation resulted in substantially reduced basal levels. A single mutation of Ser 93 to Gly present in one of the many mutant constructs characterized, mutant 25, was shown to greatly reduce the basal expression level in absence of coumermycin, but maintained an activity comparable to the wild type. This S93G mutant thus offers very desirable properties for this λR-GyrB based gene regulation system as demonstrated by read generation of stable cell lines for inducible expression of the apoptotic Bax gene. It is noteworthy that in this system, use of the strong CMV immediate-early promoter resulted in a significant higher background in comparison with the relatively weak SV40 early promoter in 293A cells (data not shown), probably due to the fact that the CMV-directed high level expression of the transactivator may have induced a concentration dependent auto-dimerization of the chimeric λR-GyrB transactivator in the cells. For this reason, we have used the SV40 early promoter for constitutively expression of the chimeric λR-GyrB transactivator. Other suitable promoters include promoters from respiratory syncytial virus (RSV), EF1, and thymine kinase (TK) genes. To increase the activation potency of the transactivator controlled by the relatively weak the SV40 early promoter, a positive regulatory feedback construct was designed by insertion of at least one, and preferably four λOP sites between the basal SV40 early promoter sequence and the CMV-derived TATA box sequences. Hence, this coumarin-regulated λR-GyrB expression system with mutated λR, such as S93G, exhibits a very high level of inducibility and demonstrates rapid and reversible on-off switching of gene expression. This system can complement the other reported regulatory systems in use and should prove to be particularly valuable for precise regulated expression of specific genes during development and in gene therapy.

To create this coumerin-regulated gene expression system, an expression cassette containing the chimeric transactivator gene is created. A transgene, the gene whose expression is to be regulated, may be included in the same expression cassette or in a separate expression cassette.

Any expression vector or integrated expression vector a may be used to create an expression cassette for this coumerin-regulated system. The cassette can be moved to any other vector for expression; particularly suitable viral vectors for this purpose include adenovirus; adeno-associated virus, retrovirus, lentivirus, and herpes simplex type I virus.

The expression cassette may be delivered into cells in vivo and in vitro, and may, with a pharmaceutically suitable carrier be delivered into humans. A person skilled in the art may select among the various vectors and other expression and delivery elements depending on such factors as the site and route of administration. For example, expression plasmid vectors in combination with transfection reagents such as liposomal and non-liposomal lipid reagents, may be directly injected into tissue or introduced by intravenous administration. Preferably, however, the expression cassette is delivered through the use of viral vectors such as adenovirus, adeno-associated virus, retrovirus, lentivirus, and herpes simplex type I virus.

The expression cassette and vector may be made available in the form of a kit, along with a pharmaceutically suitable carrier, for therapeutical treatment of a patient.

DETAILED DESCRIPTION OF THE DRAWINGS

Figure 1:
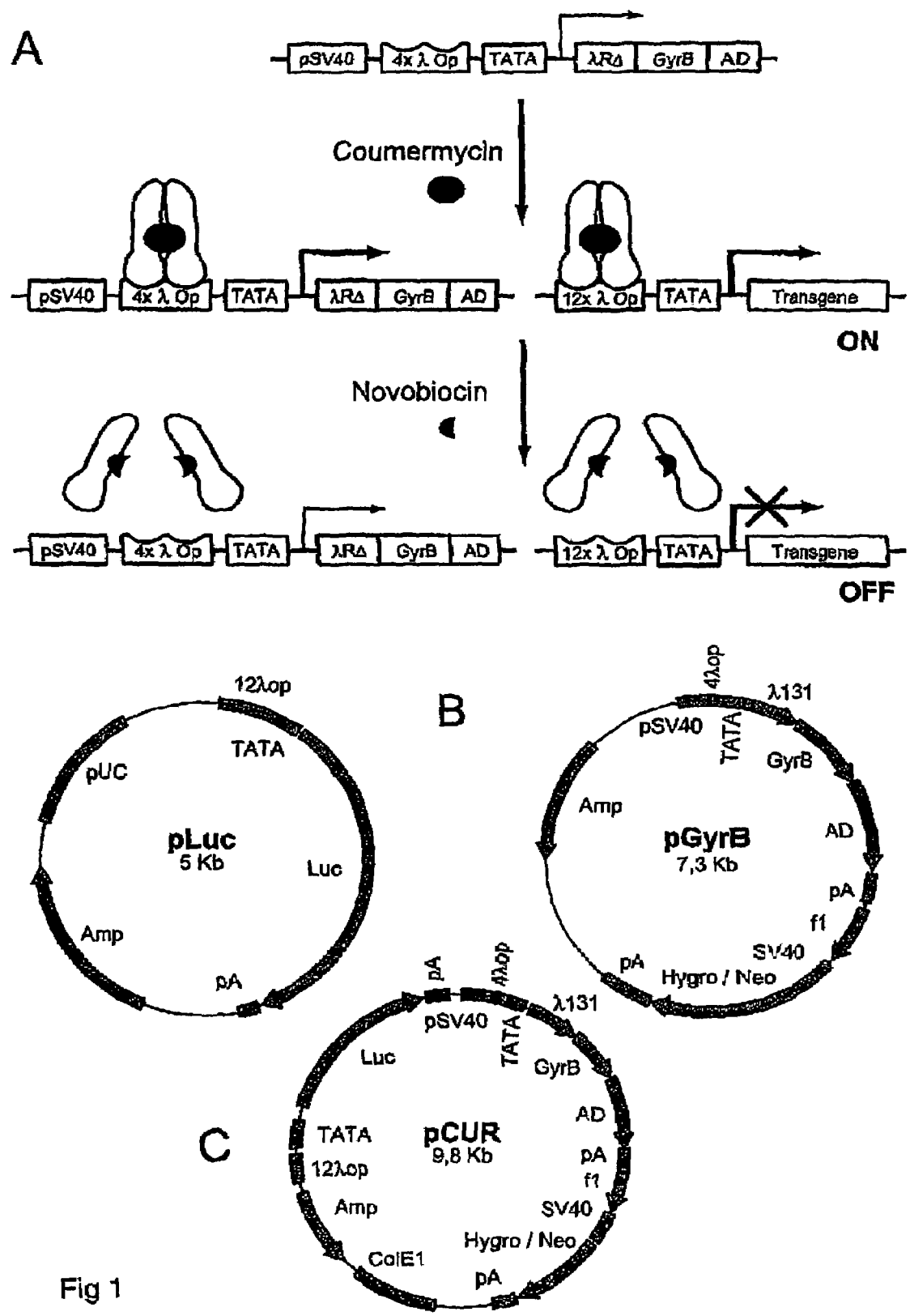
FIG. 1A is a schematic representation of the coumarin-regulated system.
FIG. 1B is a map illustrating one possible embodiment of the expression vectors.
FIG. 1C is a map illustrating a second possible embodiment of the expression vectors.

FIG. 1A. In the presence of inducer coumermycin, the constitutively produced chimeric transactivator is dimerized and bound to λOP to turn ON the transgene as well as to promptly increase the expression of the chimeric transactivator itself through execution of the activation domain (AD). Addition of novobiocin in cells causes dissociation of the dimerized transactivator to switch OFF the transgene and render the constitutive expression of the transactivator.

FIG. 1B. Two plasmids, designated pLuc and pGyrB, are designed for separate expressions of the coumerin-regulated transgene (Luc) and the transactivator λR-GyrB-AD, respectively.

FIG. 1C. The two expression cassettes for the coumerin-regulated transgene and the transactivator are built into one plasmid pLUR. TATA, the CMV mini-promoter; AD, transcription activation domain of p65-NFκB; λop, λ repressor binding site.

Figure 2:
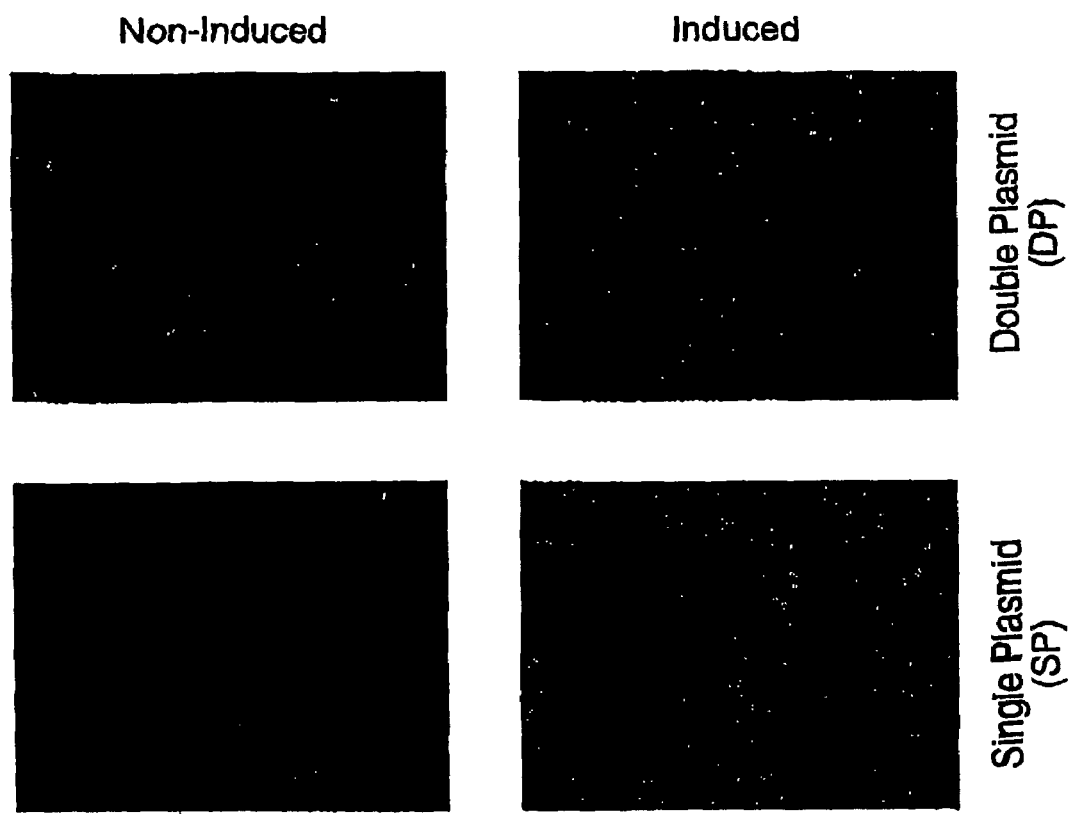
FIG. 2A shows the results after testing the ability of the double plasmid and single plasmid expression vectors to activate the GFP gene in 293A cells.
FIG. 2B shows the results after testing the ability of the double plasmid and single plasmid expression vectors to activate the luciferase gene in 293A cells.
Figure 2:
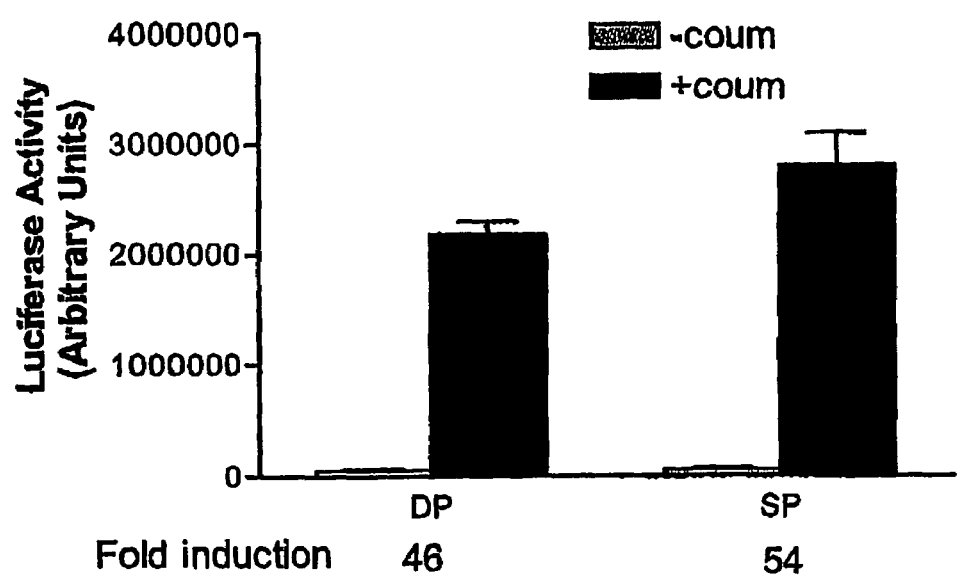

FIG. 2A. Either two plasmids pGFP and pGyrB (double plasmids, each 0.5 μg), or one plasmid pCUR (1.0 μg) containing the GFP gene (single plasmid), were transiently transfected into 293A cells. Coumermycin (5 nM) was added after 3 hr transfection and photographs were taken after additional 40 hrs.

FIG. 2B. Either two plasmids pLuc and pGyrB (DP, each 0.2 μg), or one plasmid pCUR (0.4 μg) containing the Luc gene (SP), were transiently transfected into 293A cells, respectively. Luciferase activity was measured after 40 hr induction with coumermycin (5 nM) in triplicate. The results shown are the means for triplicate determinations and representative of 3 experiments. The transfection efficiencies were normalized by co-transfection of pRL-TK vector constitutively producing *Renilla* luciferase.

Figure 3:
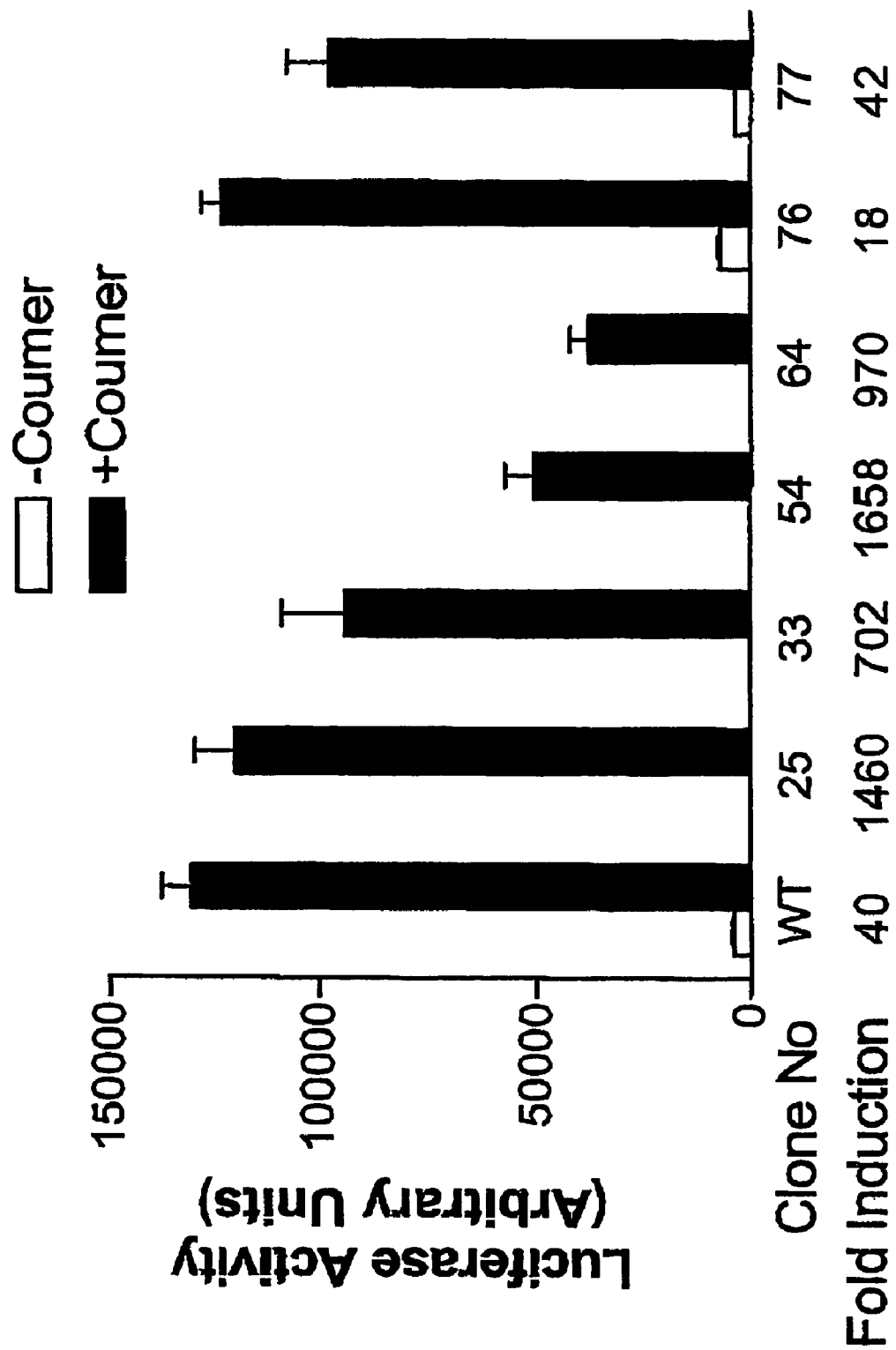
FIG. 3 shows results of an assay testing the basal activity and coumermycin-induced activity of transactivator comprising mutated λ repressor.

FIG. 3. Cells stably transfected with the reporter plasmid pLuc were transiently transfected with plasmid pGyrB (0.2 μg), either containing the wild type AR, or its mutant clone 25 (S93G), 33 (V92C/S93W), 54 (V92L/S93E), 64 (V92L/S93L), 76 (V92C/S93F) and 77 (V92T/S93T). The transfection efficiencies were normalized by co-transfection of pRL-TK vector constitutively producing *Renilla* luciferase. After 3 hr following transfection, the transfected cells were induced with coumermycin (5 nM) for 40 hr, and luciferase activities was measured from lysed cells. The results shown are the means for triplicate determinations and representative of 3 experiments.

FIG. 4A. Cells from clone 5 obtained by stably transfection with mutant S92G were induced with various concentration of coumermycin for 40 hr.

FIG. 4B. The same cells were induced with 5 nM coumermycin for various times as indicated. Results represent two independent experiments performed in triplicate.

FIG. 5A. Cells of stable clone S93G-5 were induced with 5 nM coumermycin together with various concentration of novobiocin for 40 hr and luciferase activity was measured. Results represent two independent experiments performed in triplicate.

FIG. 5B. Cells of stable clone S93G-5 were induced with coumermycin for 11 hr first, and then novobiocin was added to a final concentration of 2.5 µM. At different points of time, cells were collected for luciferase activity assay. Results shown are the means for triplicate determinations and representative of 3 experiments.

Figure 6:
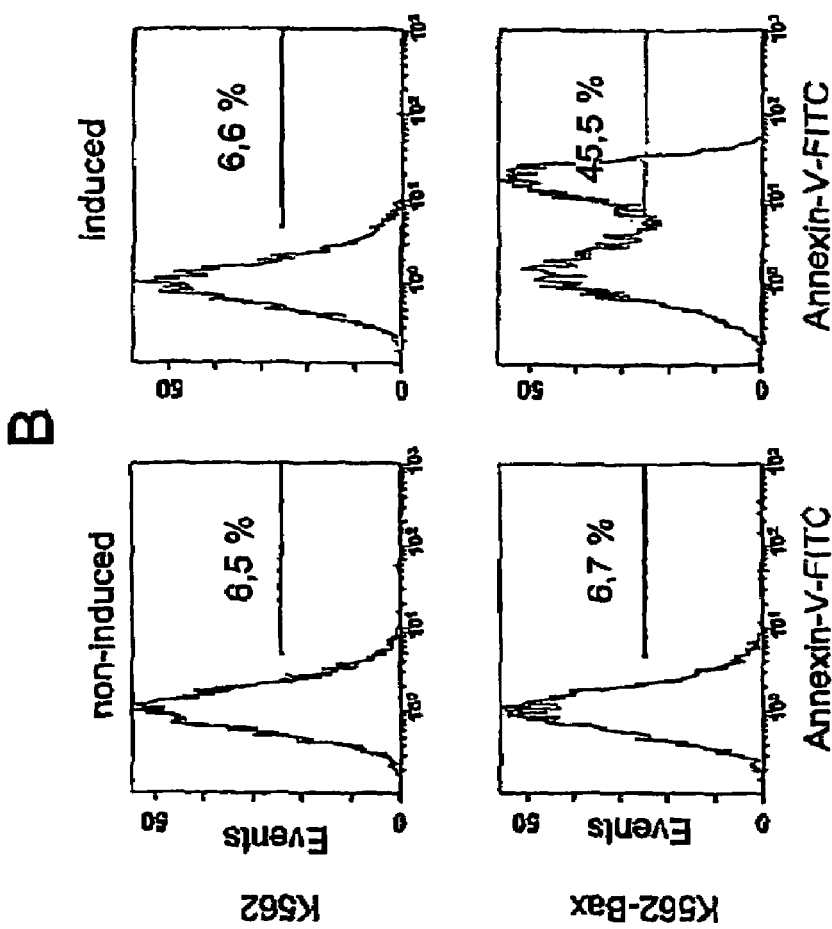
FIG. 6A shows a Western blot analysis of cell lysate and cytosol protein fraction from k562 cells with and without coumermycin treatment.
FIG. 6B shows a flow cytometric analysis of k562 cells with and without coumermycin treatment.
Figure 6:
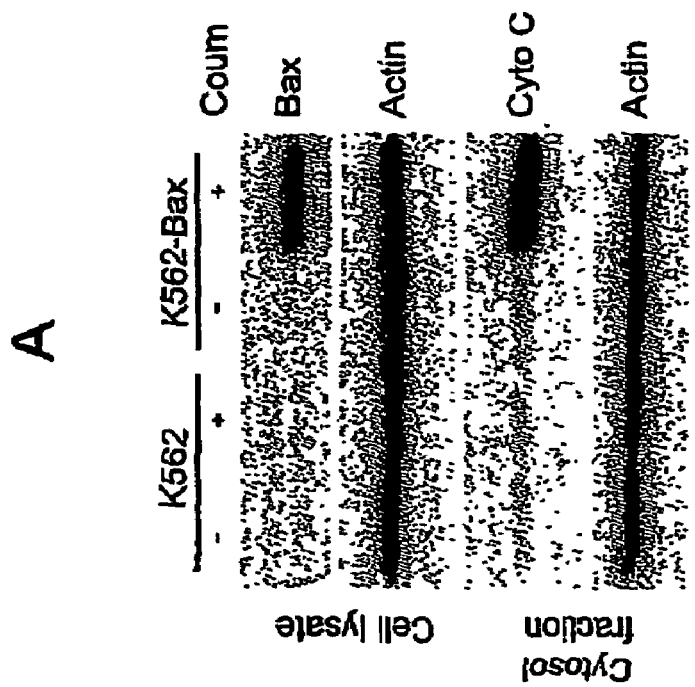

FIG. 6A. Clone K562-Bax 65, which was obtained from stably transfection with two plasmids pGyrB and pBax, was used. Cells were induced for 36 hr with coumermycin (5 nM). Western blot analysis was performed in cytosol protein fraction (30 µg) of the cells with a mouse anti-cytochrome C monoclonal antibody (Lower panel) or in whole cell extracts from $5 \times 10^5$ cells with a rabbit polyclonal anti-mouse Bax antibody specifically reactive to mouse Bax (Upper panel).

FIG. 6B. Flow cytometric analysis of apoptotic K562-Bax cells and K562 wild type cells were performed with and without coumermycin treatment for 36 hr.

PROCEDURES AND EXAMPLES

Cell Culture, Medium, and Chemicals

Human embryonic kidney 293A cells (ATCC) were maintained in DMEM medium, supplemented with 10% fetal bovine serum at 37° C. in 5% $CO_2$. Human chronic myelogenous leukemia K562 cells (ATCC) were maintained in RPMI1640 medium, supplemented with 2.0 mM L-glutamine, and 10% fetal bovine serum at 37° C. in 5% $CO_2$. Stable 293A cell lines were selected or maintained in either 200 or 150 µg/ml hygromycin B (Invitrogen) respectively and 1200 or 600 µg/ml G418 (MultiCell) respectively. K562 stable cell lines were selected and maintained in 400 µg/ml hygromycin B.

Construction of the Coumarin-Responsive Expression Cassette pLuc, pGFP and pBax

The mini promoter sequence from the immediate-early gene of human cytomegalovirus (CMV*) was amplified by PCR from pUHD 10-3 vector (13) with a sense primer containing XbaI site and the anti-sense primer containing restriction sites, AscI and HpaI. The amplified sequence was inserted into pG5CAT (Clontech) at the XbaI and HpaI sites, producing pG5CMV*. The green fluorescent protein (GEP) gene was PCR amplified from pEGFP-C1 (Clontech) and inserted into pG5CMV*, resulting in pG5CMV*-GFP. Four and 12 copies of λ operator domain (4×λOP and 12×λOP) (14) were generated by annealing and multiple self-ligation of two synthetic oligonucleotide: 5'-TCGAGTTTAC-CTCTGGCGGTGATAG-3' (SEQ. ID NO. 9) and 5'-TC-GACTATCAC CGCCAG AGGTAAAC-3' (SEQ ID NO. 10). The multiple self-ligated product was selected from 4 and 12 copies of λOP and digested with XhoI and SalI, and cloned into pG5CMV*-GFP at the same sites to produce 4×λopGFP and 12×λopGFP (pGFP). The firefly luciferase (Luc) coding sequence (accession M15077) was PCR amplified from Luc vector (Promega). The amplified product was cloned into p12×λopGFP at AscI and HpaI, resulting in pLuc (SEQ ID NO. 29). Similarly, the mouse Bax coding sequence (accession L22472) was PCR amplified and cloned into p12× λopGFP at AscI and HpaI, resulting in pBax.

Construction of the Expression Cassette for the Chimeric λR-GyrB Transactivator

To construct the pcDNA3-λR-GyrB transactivator with neomycin or hygromycin as a selection marker, the N-terminal DNA binding domain (residues 1-131) of the bacteriophage λ repressor (λR)(10) was PCR amplified and cloned into pcDNA3 (Invitrogen) at HindIII (klenow blunted) and EcoRV sites, producing pcDNA3λR131. The amino-terminal 24K subdomain bacterial DNA gyrase B subunit (GyrB)(8) was PCR amplified from the genomic DNA of Escherichia coil DH 5α strain to produce pGEMT-GyrB. The p65 NFκB activation domain ($AD_{NF\kappa B}$) was PCR amplified with appropriate restriction sites in the primers from pCMV-AD vector (Stratagene). The amplified product was cloned into pGEMT-GyrB at NcoI and XbaI, producing pGEMT-GyrB-NFκB that was further cloned into PcDNA3-λR131 at EcoRV and XbaI sites. The resultant plasmid was designated pcDNA3-λR131-GyrB-NFκB. To construct the SV40 promoter-directed coumarin-responsive expression cassette, 4×λop together with the mini CMV* promoter (13) was amplified by PCR from the 4×λopGFP with appropriate primers. The amplified fragment was cloned into the NcoI and SmaI sites of the pM vector (Clontech), which contains the SV40 early promoter (15), producing pMSV40e-4×λop-CMV*. The ΔR131-GyrB-NFκB cassette was PCR amplified from pcDNA3-λR131-GyrB-NFκB, and cloned into pMSV40e-4×λop-CMV* to produce pMSV40e-4×λop-CMV*-λR131-GyrB-NFκB, named pGyrB.

Construction of pCUR Containing the Coumarin-Regulated Two Gene Expression Cassette To construct one plasmid containing both the expression cassette for the chimeric λR-GyrB transactivator and the expression cassette for coumarin-responsive gene, the SV40e-4×λop-λR131 fragment was isolated from pMSV40e4×λop-λR131-GyrB-NFκB following digestion with AatII blunt and EcoRV, and cloned into pcDNA3-λR131-GyrB-NFκB at NruI and EcoRV sites, producing pcDNA3-SV40e-4×λop-λR131-GyrB-NFκB. Next, the 12×λopLuc fragment was isolated from Pluc by SmaI digestion, and cloned into pcDNA3-SV40e-4×λop-λR131-GyrB-NFκB at NdeI blunt, producing pcDNA3-12×λopLuc-SV40e-4×λop-λR131-GyrB-NFκB, which was designated pCUR.

Mutagenesis of the λ Repressor 131 DNA Binding Domain

Amino acid substitutions in the λ131 DNA binding domain at residues 85, 92 and 93, were performed as recommended by the manufacturer of the QuikChange™ Site-Directed Mutagenesis Kit (Stratagene). Briefly, two complimentary 42 bp specific primers covering residues 85, 92 and 93 were synthesized containing a VNN (V=A, C, G and N=A, C, G, T) codon for each of the 85, 92 and 93 residues. Standard thermocycling reactions were performed using Pfu Turbo (Stratagene) with the template DNA of pcDNA3-λR131-GyrB-ADNFκB. The PCR product was fully digested with DpnI and transformed into XL2-Blue (Stratagene). Single colonies were isolated and sequenced to define amino acid substitutions. Mutant clones were primarily screened by transient co-transfection with pGFP to evaluate inducibilities and background fluorescence intensities. Suitable candidates were further evaluated by transient or stable co-transfection with pLuc into 293A cells to fully characterize their inducible capability and basal expression levels.

Stable Cell Line Production and Luciferase Assays

Exponentially growing 293A cells were seeded at $8 \times 10^5$ in 60 mm dishes the day prior to transfection and co-transfected with 5 µg of XmnI linearized pLuc and 0.2 µg of pcDNA3.1 hygromycin using the SuperFect kit (Qiagen). Alternatively, the cells were transfected with PvuI linearized pCUR. Two days following transfection, the cells were replaced into 100 mm dishes, and selected with appropriate antibiotics for 2 weeks. Single clone was selected for further assay. To assay Luc activity, $1 \times 10^5$ cells were seeded in a 24-well plate (Corning Inc. Costar) and induced immediately with 5 nM coumermycin. After 40 hrs induction, cells were lysed in 100 µl lysis buffer (Promega) for 20 min. Luc activity was determined using 20 µl of total cell lysate using the Dual-Luciferase Reporter Assay System (Promega). The reporter firefly luciferase activities were measured and normalized by the transfection efficiencies estimated by the activities of Renilla luciferase constitutively expressed from cotransfected pRL-TK. For inducible expression of the Bax gene, wild-type K562 cells were transfected using electroporlation with 5 µg DNA of the linearized pBax and pGyrB. Cell lines were selected with hygromycin and positive clones were screened in the induced and non-induced states using anti-Bax antibody visualized by Western blot.

Preparation of Cytosolic Extract and Immunoblotting

K562 ($10^6$) wild type and K562 cells ($10^6$), which were stably transfected with pBax and pGyrB, were seeded in 35 mm dishes and induced with 5 nM coumermycin. For immunoblotting, 36 hrs following induction the cells were lysed with 2x loading buffer at 100° C. for 5 minutes. For cytosolic extraction, cells ($10^7$) were seeded and after 36 hrs induction the cells were washed twice with cold PBS (MultiCell) followed by centrifugation at 200×g for 5 min. The cell pellets were resuspended in 300 µl of extraction buffer containing 220 mM mannitol, 68 mM sucrose, 50 mM Pipes-KOH, pH 7.4, 50 mM KCL, 5 mM EGTA, 2 mM $MgCl_2$, 1 mM EDTA, 1 mM dithiothreito, and protease inhibitors. After 30 min incubation on ice, cells were homogenized using a glass dounce and a B pestle for 80 strokes. Homogenized cells were spun at 14,000×g for 15 min, and the supernatant was removed and stored at −80° C. until for SDS polyacrylamide gel electrophoresis. Cyctosolic protein extract (30 µg) was boiled for 5 min and electrophoresed on a 15% SDS-polyacrylamide gel. The proteins were transferred to nitrocellulose membrane (Hybond ECL) and blocked in 10% nonfat milk/TBST (10 mM Tris-HCl, pH 8.0, 150 mM NaCl, 0.05% Tween 20) for 1 h at room temperature. The membrane was probed with either a rabbit polyclonal anti-mouse Bax anti body (Santa Cruz Biotechnology) that appeared to specifically react to mouse Bax as previously reported (16) or with a mouse anti-cytochrome C monoclonal antibody (BD pharMingen Technical). The secondary antibody was conjugated with horseradish peroxidase.

Flowcytometry

Cells ($10^6$) in 35 mm dishes were treated with 5 nM coumermycin for 36 hours and then stained for apoptosis detection using the Annexin-V-Flous staining kit (Roche, Mannheim). The analysis was performed on 10,000 cells using a Coulter EPICS™ XL-MCL flowcytometer (Beckman-Coulter, Hieleah, Fla.) equipped with 15 mW at 488 nm argon ion laser as an excitation source. Total cell population was selected using forward scattering and side scattering parameters with a 488 nm dichroic long pass filter. The FITC green fluorescence emission was detected using a 550 nm dichroic long pass and a 525 nm band pass filter set. Red fluorescence from Propidium Iodide stained cells was detected using a 645 nm dichroic long pass and a 620 nm band pass filter set.

Example 1

Constructs for Expression of the Chimeric λR-GyrB Transactivator and the Target Transgenes To construct a coumarin-regulated gene expression system, the N-terminal domain of the bacterial phage λ repressor (λR) (codons 1-131) (SEQ ID NOS. 7 and 8) was fused to the GyrB domain (codons 2-220 of bacterial DNA gyrase) (SEQ ID NOS. 3 and 4). A transcription activation domain, p65 NFκB, was further fused to the C-terminus of the GyrB domain to make a chimeric transactivator. Expression of the chimeric transactivator is controlled by a hybrid promoter consisting of the basal SV40 early promoter sequence up to −52 (15) and a TATA box from the CMV promoter (13). In addition, four binding sites of λ operator (λOP) were inserted between the SV40 and the TATA box sequences. To regulate transgene expression, twelve copies of the λ operator (λOP) site (14) were placed directly upstream of the CMV mini-promoter (13) to control downstream gene expression. In this regulator system, the hybrid SV40-CMV promoter constitutively directs a moderate expression of the chimeric transactivator in cells. Addition of coumermycin induces dimerization of the transactivator, resulting in binding of λR to the λOP sites, thus increasing the production of the transactivator in a manner of positive regulatory feedback and activating the expression of the target transgene. The transactivator dimers induced by coumermycin can be dissociated by addition of novobiocin, thereby immediately turning off expression of the transgene (FIG. 1A). The expression cassette for the chimeric transactivator and the coumermycin/novobiocin-responsive transgene expression cassette, containing the reporter gene (Luc or GFP), are either built into two separate plasmids, pLuc and pGyrB (FIG. 1B), for co-transfection or for two-stage establishment of stable cell lines, or built into one plasmid (pCUR) for convenient one-stage establishment of inducible lines (FIG. 1C).

Example 2

Coumermycin-Dependent Functional Characterization of the Chimeric λR-GyrB Transactivator To examine whether the chimeric transactivator λR-GyrB-NFκB is coumermycin-responsive for induction of gene expression, we cloned two reporter genes, encoding luciferase (Luc) and green fluorescent protein (GFP) into the transgene expression cassette of both the two-plasmid- and one-plasmid-inducible expression systems. The constructs were transiently transfected into HEK 293A cells. The transfected cells were induced by addition of coumermycin for 40 hrs. As shown in FIG. 2A, GFP expression was greatly induced for both systems in 293A cells. Similar results were observed with reporter luciferase (FIG. 2B). The inducibilities of luciferase activity in both cassettes are comparable, around 50-fold induction. This moderate inducibility in this regulatory system may be explained at least in part by its relatively high basal activity as indicated by a low, but apparent expression of GFP in the absence of coumermycin (FIG. 2A).

Example 3

Mutation of the λ Repressor DNA Binding Domain for Elimination of its Intrinsic Dimerization In order to improve the induction efficiency of this λR-GyrB based regulatory system, efforts were made to minimize its basal expression level. It is known that although the C-terminal domain of λR, residues 132-236, is mainly responsible for mediating the homodimerization of the repressor, residues in helix 5 in the N-terminal domain, such as Ile-85, Val-92 and Ser-93, are also involved in dimerization for binding of λR to the operator (12). The observed basal activity of transactivator λR-GyrB-NFκB in 293A cells is likely contributed by the helix5-helix5 interaction. To reduce the basal activity of this inducible system, we performed a PCR-based random mutagenesis for each residue of Ile-85, Val-92 and Ser-93 potentially involved in the helix5-helix5 interaction of λR. Over one hundred potential mutant constructs in pGyrB located in the λR-GyrB-NFκB transactivator were generated and transiently transfected with the coumarin responsive luciferase reporter gene (pLuc) into 293A cells for evaluation of their basal expression levels and inducibilities. Dramatic variation was observed in the activities of these mutants in response to coumermycin. In general, the identified mutants in these three sites displayed less activity in induction when compared with parental. However, the basal expression levels of most mutants were significantly lower than that of the wild type. After comparing their inducibilities, seven mutant constructs, namely clone 25 (S93G), 33 (V92C and S93W), 54 (V92L and S93E), 64 (V91L and S92L), 76 (V92C and S93F), and 77 (V92T and S93T) (see Table I), were chosen for further study of their capabilities for induction. For this, these constructs were transiently transfected into 293A cells in which the coumarin responsive luciferase reporter gene was stably transfected. Luciferase activity was measured in transfected cells treated with coumermycin. As shown in FIG. 3, although nearly all of these mutants displayed some reduction in activity in response to coumermycin, the magnitude of induction for most of these mutants was significantly increased due to reduction of their basal expression levels from the wild type. Most notably mutant S93G (#25) exhibited an inducible activity comparable to the wild type, and a very low basal expression level, resulting in a 1,460-fold induction. Similar results were observed in HeLa cells (data not shown). To further characterize this mutant, S93G-mutated chimeric transactivator was integrated into plasmid pCUR for one-stage establishment of inducible lines in 293A cells. Stable clones were selected and analyzed for their responsiveness to coumermycin. All 50 stable clones tested were coumermycin responsive with varied inducible activities. Luciferase activity assays revealed that the magnitude of induction was over three orders in approximately 30% of coumermycin responsive clones isolated due to very low basal expression levels. Of particular interest were clones 23 and 44, which exhibited over 10,000-fold induction following coumermycin treatment (Table II).

TABLE I

| | Mutation in λ represser | | |
|---|---|---|---|
| Clone | Amino acid exchanges | | |
| Wild type | Ile 85 | Val 92 | Ser 93 |
| 25 | | | Gly |
| 33 | | Cys | Trp |
| 54 | | Leu | Glu |
| 64 | | Leu | Leu |
| 76 | | Cys | Phe |
| 77 | | Thr | Thr |

The three residues, Ile 85, Val 92 and Ser 93 of λ repressor, were randomly mutated. Seven mutant constructs with amino acid substitutions as listed exhibited high inducibilities and were chosen for characterization.

TABLE II

Coumermycin-dependent luciferase activity of different clones

| | Luciferase Activity (Arbitrary Light Units/µg protein) | | |
|---|---|---|---|
| Clone | Without Coum | With Coum | Activation factor |
| 5 | 9.4 ± 0.7 | 47,460 ± 447 | $5.1 \times 10^3$ |
| 8 | 35.8 ± 9.2 | 52,408 ± 2,254 | $1.5 \times 10^3$ |
| 10 | 0.5 ± 0.1 | 1,591 ± 100 | $3.2 \times 10^3$ |
| 18 | 1.3 ± 0.4 | 7,446 ± 36 | $5.8 \times 10^3$ |
| 23 | 0.6 ± 0.1 | 8,237 ± 204 | $1.4 \times 10^4$ |
| 28 | 2.4 ± 0.2 | 12,292 ± 550 | $5.1 \times 10^3$ |
| 34 | 8.1 ± 0.9 | 46,980 ± 1,300 | $5.8 \times 10^3$ |
| 44 | 2.4 ± 0.6 | 30151 ± 2020 | $1.3 \times 10^4$ |
| 45 | 1.2 ± 0.2 | 1,909 ± 24 | $1.6 \times 10^3$ |
| 47 | 4.1 ± 0.5 | 8,528 ± 43 | $2.1 \times 10^3$ |

Cells were stably transfected with pCUR containing the Luc gene. All of neomycin-resistant 50 clones tested were coumermycin-responsive. Ten clones with high inductions were chosen to characterize their inducibility in absence and presence of coumermycin (5 nM) through luciferase activity assay. Values are means of three independent luciferase determinations from three independently cell cultures.

Example 4

Coumermycin Responsiveness in Stable Cell Lines and Ready Switch-Off of the Induced Expression by Novobiocin The kinetic characteristics of this inducible system were further examined in stable cell lines. To study the dose-responsiveness of expression, the luciferase activity of cells treated for 40 hrs with varying concentration of coumermycin was assayed in a stable cell clone S93G-5 that displays a medium inducibility. As shown in FIG. 4A, luciferase expression was induced by coumermycin in a dose-dependent manner. Apparent induction of luciferase expression was observed at a concentration of the antibiotic as low as 0.5 nM (approximately 0.5 ng/ml). Maximal induction was achieved at a concentration of 2.5-5 nM coumermycin. The inducibility of coumermycin was decreased at 50 nM concentration, hence a fairly broad dosage range (more than 10-fold) is available for induction with this drug. Appreciable luciferase activity was detected after 5 hr induction (data not shown), and the maximal inducibility was observed after 24 hr-induction (FIG. 4B).

To study whether novobiocin, the monomer of coumermycin, is able to switch off the coumermycin-induced expression of luciferase, various concentrations of novobiocin were incubated together with 5 nM coumermycin in 293A cells for 40 hr. Luciferase activity assay revealed that the coumermycin-induced expression of luciferase was effectively inhibited in a dose-dependent manner. At a concentration of 5 μM novobiocin, however, over 98% of the coumermycin-induced luciferase expression was suppressed (FIG. 5A). It should be noted that coumermycin at 10 μM concentration and novobiocin at 25 μM concentration do not exert any detectable cellular toxicity as judged by cell growth rate and transient expression of transfected CMV-GFP construct in the cells (data not shown). To further demonstrate the switch-off capability of novobiocin for this inducible system, clone S93G-5 cells were induced with 5 nM coumermycin for 11 hr, after which novobiocin was added into the culture to 2.5 μM concentration. The luciferase assay showed that while luciferase activity continuously increased for a period of more than 24 hr in the control culture, novobiocin at a concentration of 2.5 μM nearly completely switched off the coumermycin-induced expression of luciferase in less than 4 hr following its administration (FIG. 4B). These results clearly demonstrated that novobiocin is a suitable antagonist of coumermycin for rapid and effective shutdown of transgene expression in this inducible system.

Example 5

Tightly Regulated Expression of the Apoptotic Gene BAX in k562 Cells With the Mutated Chimeric Transactivator It has been reported that high-level expression of Bax (Bcl2-associated X protein) elicits apoptosis in a variety of human cancer cells (17). In malignant hematopoietic cells, including k562, Bax overexpression leads to apoptosis of the transfected cells through cytochrome C release (18). To evaluate the tightness of gene expression regulated by the chimeric transactivator, the apoptotic Bax gene was cloned into the transgene-expression cassette from the two-plasmid induction system previously described. Both wild type and S93G mutant transactivator in plasmid pGyrB were co-transfected with pBax plasmid into K562 cells. Stable clones harboring the both plasmids were isolated and characterized following induction. Western blot analysis revealed that clones with highly inducible expression of Bax were hardly identified among the wild type transactivator-transfected cells as the majority of isolated clones displayed either no additional inducible or poorly inducible expression of Bax (data not shown). However, clones with highly inducible expression of Bax were readily isolated from cells transfected with the transactivator mutant S93G. As shown in FIG. 6A from one representative clone S93G-Bax 65, Bax expression was greatly induced in the cells treated with coumermycin for 36 hr. Concomitantly, cytochrome c was released in substantial amounts from mitochondria in response to coumermycin treatment for 36 hr. Fluorescence-activated cell sorter (FACS) analysis consistently confirmed that while the drug did not induce additional cell death in parental cells (FIG. 6B, upper panel) treatment of S93G-Bax 65 cells with coumermycin increased the fraction of apoptotic cells from 6.7% to 45.5% (FIG. 6B, lower panel), a result comparable to that observed in the Tet-system (18). These results demonstrate that this system with mutated S93G transactivator is tightly regulated by coumermycin to express the apoptosis-inducing gene in mammalian cells.

Abbreviations: GFP, green fluorescent protein; GyrB, bacterial DNA gyrase B subunit; CMV, human cytomegalovirus; λR, λ repressor; λOP, λ operator; FACS, fluorescence-activated cell sorter;

REFERENCES

1. Saez, E., No, D., West, A., and Evens, R. M. (1997) *Curr. Opin. Biotehcnol.* 6, 608-611.
2. Harvey, D., and Caskey, C. (1998) *Curr. Opin. Chem.* 2, 512-518.
3. Gingrich, J., and Roder, J. (1998) *Annu. Rev. Nueurosci.* 21, 377-405.
4. DeMayo, F. J., and Tsai, S. Y. (2001) *Trends Endocrinol. Metab.* 12, 348-353.
5. Urlinger, S., Baron, U., Thellmanni, M., Hasan, M. T., Bujard, H., and Hillen, W. (2000) *Proc. Natl. Acad. Sci. U.S.A.* 97, 7963-7968.
6. Riond, J. L., and Riviere, J. E. (1988) *Vet. Human Toxicol.* 5, 431-443.
7. Farrar, M. A., Qlson, S. H., and Perlmutter, R. M. (2000) *Methods Enzymol* 327, 421-429.
8. Gilbert, E. J., and Maxwell, A. (1994) *Mol microbiol* 12, 365-373.
9. Ali, J. A., Jackson, A. P., Howells, A. J., and Maxwell, A. (1993) *Biochemistry,* 32, 2717-2724.
10. Hu, J. C., O'Shea, E. K., Kim, P. S., and Sauer, R. T. (1990) *Science* 250, 1400-1402.
11. Pabo, C. O., Sauer, R. T., Sturtevant, J. M., and Ptashne, M. (1979) *Proc. Natl. Acad. Sci. U.S.A.* 76, 1608-1612.
12. Weiss, M. A., Pabo, C. O., Karplus, M., and Sauer, R. T. (1987) *Biochemistry* 26, 897-904.
13. Gossen, M., and bujard, H. (1992) *Proc. Natl. Acad. Sci; U.S.A.* 89, 5547-5551.
14. Kim, Y. I., and Hu, J. C. (1995) *Proc. Natl. Acad. Sci. U.S.A.* 92, 7510-7514.
15. Byrne, B. J., Davis, M. S., Yamaguchi, J., Bergsma, D. J., and Subramanian, K. N. (1983) *Proc. Natl. Acad. Sci. U.S.A.* 80, 721-725.
16. Pastorino, J. G., Chen, S.-T., Tafani, M., Snyder, J. W., and Farber J. L. (1998) *J. Biol. Chem.* 273, 7770-7775.
17. Gu, J., Zhang, L., Huang, X., Lin, T., Yin, M., Xu, K., Ji, L., Roth, J. A., and Fang, B. (2002) *Oncogene* 21, 4757-4764.
18. Kobayashi, T., Sawa, H., Morikawa, J., Ueno, S., Katayama, N., Zhang, W., and Shiku, H. (2002) *Int J Oncol.* 20, 723-728.
19. O'Farrell; A. M., Liu, Y., Moore, K W., and Mui, A. L. (1998) *EMBO J.* 17, 1006-1018.
20. Gormley, N. A., Orphanides, G., Meyer, A., Cullis, P. M., and Maxwell, A. (1996) *Biochemistry* 35, 5083-5092.
21. Godfrey J. C., and Price, K. E. (1972) *Adv. Appl. Microbiol.* 15, 231-296.
22. Eder, J. P., Wheeler, C. A. Teicher, B. A., and Schnipper, L. E. (1991) *Cancer Res.* 52, 510-513.
23. Chrast-Balz, J., and Van huijsduijnen, R. H. (1996) *Nucleic Acids Res.,* 24, 2900-2904.
24. Farrar, M. A., Alberola-Lla, J., and Perlmutter, R. M. (1996) *Nature,* 383, 178-181.

We claim:

1. A nucleic acid molecule encoding a biologically active chimeric transactivator protein comprising:
   a) a functional DNA binding domain of a bacteriophage λ repressor protein, comprising amino acids 1-131 thereof (SEQ ID NO.: 8) and further comprising an amino acid mutation at at least one position selected from V92 and S93, such that the binding domain is not capable of dimerization;
   b) bacterial DNA gyrase B subunit (Gyr B); and
   c) a transcription activation domain.

2. A nucleic acid molecule as claimed in claim 1 wherein the transcription activation domain is selected from the group consisting of NFκB p65, VP16, B42 and Gal4.

3. A nucleic acid molecule as claimed in claim 1 wherein the transcription activation domain is a transcription activation domain from NFκB.

4. A nucleic acid molecule as claimed in claim 1 wherein the bacterial DNA gyrase B subunit comprises the amino acid sequence set forth as SEQ ID NO.: 4.

5. A nucleic acid molecule as claimed in claim 1 wherein the mutation of λ repressor is selected from the group consisting of V92C and S93W; V92L and S93E; V92L and S93L and S93G.

6. A nucleic acid molecule as claimed in claim 1 wherein the mutation of λ repressor is S93G.

7. An expression vector comprising a nucleic acid molecule according to claim 1 operatively linked to an expression control sequence.

8. An expression vector as claimed in claim 7, wherein the expression control sequence comprises a constitutive promoter.

9. An expression vector as claimed in claim 8, wherein said promoter is selected from the group consisting of promoters from SV40, human cytomegalovirus (CMV), respiratory syncytial virus (RSV), EF1, and thymine kinase (TK) genes.

10. An expression vector as claimed in claim 8, wherein said promoter is SV40.

11. An expression vector as claimed in claim 10, wherein said SV40 promoter further comprises a CMV promoter TATA box.

12. An expression vector as claimed in claim 7, wherein the expression control sequence comprises at least one operator sequence that is recognized by the DNA binding domain of the bacteriophage λ repressor protein.

13. An expression vector as claimed in claim 12, wherein said at least one operator sequence is a bacteriophage A operator sequence.

14. An expression vector as claimed in claim 7, further comprising a target gene.

15. An expression vector as claimed in claim 14, wherein said target gene encodes a protein with therapeutic action.

16. An expression vector as claimed in claim 14, wherein said target gene is operatively linked to at least one operator sequence that is recognized by the DNA binding domain of the bacteriophage λ repressor protein.

17. An expression vector as claimed in claim 16, wherein said at least one operator sequence is a bacteriophage A operator sequence.

18. An expression vector as claimed in claim 7, wherein the vector is a plasmid vector.

19. An expression vector as claimed in claim 7, wherein the vector is a viral vector.

20. An expression vector as claimed in claim 19, wherein the viral vector is selected from the group consisting of adenovirus vectors, adeno-associated virus vectors, retrovirus vectors, lentivirus vectors, and herpes simplex type I virus vectors.

21. A host cell comprising an expression vector as claimed in claim 7.

22. A host cell as claimed in claim 21, the host cell being selected from a group consisting of endothelial cells, lymphocytes, macrophages, hematopoietic cells, fibroblasts, muscle cells, liver cells, kidney cells, epithelial cells of the gastrointestinal tract, of the respiratory system, of the lower urinary tract, of the sexual organs, of the skin, glia cells, cells of the nervous system, tumour cells and leukemia cells.

23. A pharmaceutical composition comprising an expression vector according to claim 7 and a pharmaceutically acceptable carrier.

24. An expression vector as claimed in claim 7 which is administered externally, perorally, intravesicularly, nasally, intrabronchially or into the gastrointestinal tract, or which is injected into an organ, into a body cavity, into the muscle system, subcutaneously or into the blood circulation, for the prophylaxis or therapy of a disease.

25. A kit comprising an expression vector as claimed in claim 7 and a pharmaceutically suitable carrier, wherein said expression vector is administered externally, perorally, intravesicularly, nasally, introbronchially or into the gastrointestinal tract, or which is injected into an organ, into a body cavity, into the muscle system, subcutaneously or into the blood circulation, for the prophylaxis or therapy of a disease.

26. A host cell as claimed in claim 21, capable of activating transcription of a target gene upon exposure to coumermycin and capable of deactivating transcription of the target gene upon exposure to novobiocin.

* * * * *

SEQUENCE LISTING

<160> NUMBER OF SEQ ID NOS: 10

<210> SEQ ID NO 1
<211> LENGTH: 2412
<212> TYPE: DNA
<213> ORGANISM: Escherichia coli
<220> FEATURE:
<221> NAME/KEY: CDS
<222> LOCATION: (1)..(2412)

<400> SEQUENCE: 1

```
atg tcg aat tct tat gac tcc tcc agt atc aaa gtc ctg aaa ggg ctg       48
Met Ser Asn Ser Tyr Asp Ser Ser Ser Ile Lys Val Leu Lys Gly Leu
 1               5                  10                  15 gat gcg gtg cgt aag cgc ccg ggt atg tat atc ggc gac acg gat gac       96
Asp Ala Val Arg Lys Arg Pro Gly Met Tyr Ile Gly Asp Thr Asp Asp
                 20                  25                  30 ggc acc ggt ctg cac cac atg gta ttc gag gtg gta gat aac gct atc      144
Gly Thr Gly Leu His His Met Val Phe Glu Val Val Asp Asn Ala Ile
             35                  40                  45 gac gaa gcg ctc gcg ggt cac tgt aaa gaa att atc gtc acc att cac      192
Asp Glu Ala Leu Ala Gly His Cys Lys Glu Ile Ile Val Thr Ile His
 50                  55                  60 gcc gat aac tct gtc tct gta cag gat gac ggg cgc ggc att ccg acc      240
Ala Asp Asn Ser Val Ser Val Gln Asp Asp Gly Arg Gly Ile Pro Thr
 65                  70                  75                  80 ggt att cac ccg gaa gag ggc gta tcg gcg gcg gaa gtg atc atg acc      288
Gly Ile His Pro Glu Glu Gly Val Ser Ala Ala Glu Val Ile Met Thr
                 85                  90                  95 gtt ctg cac gca ggc ggt aaa ttt gac gat aac tcc tat aaa gtg tcc      336
Val Leu His Ala Gly Gly Lys Phe Asp Asp Asn Ser Tyr Lys Val Ser
                100                 105                 110 ggc ggt ctg cac ggc gtt ggt gtt tcg gta gta aac gcc ctg tcg caa      384
Gly Gly Leu His Gly Val Gly Val Ser Val Val Asn Ala Leu Ser Gln
            115                 120                 125 aaa ctg gag ctg gtt atc cag cgc gag ggt aaa att cac cgt cag atc      432
Lys Leu Glu Leu Val Ile Gln Arg Glu Gly Lys Ile His Arg Gln Ile
        130                 135                 140 tac gaa cac ggt gta ccg cag gcc ccg ctg gcg gtt acc ggc gag act      480
Tyr Glu His Gly Val Pro Gln Ala Pro Leu Ala Val Thr Gly Glu Thr
145                 150                 155                 160 gaa aaa acc ggc acc atg gtg cgt ttc tgg ccc agc ctc gaa acc ttc      528
Glu Lys Thr Gly Thr Met Val Arg Phe Trp Pro Ser Leu Glu Thr Phe
                165                 170                 175 acc aat gtg acc gag ttc gaa tat gaa att ctg gcg aaa cgt ctg cgt      576
Thr Asn Val Thr Glu Phe Glu Tyr Glu Ile Leu Ala Lys Arg Leu Arg
                180                 185                 190 gag ttg tcg ttc ctc aac tcc ggc gtt tcc att cgt ctg cgc gac aag      624
Glu Leu Ser Phe Leu Asn Ser Gly Val Ser Ile Arg Leu Arg Asp Lys
            195                 200                 205 cgc gac ggc aaa gaa gac cac ttc cac tat gaa ggc ggc atc aag gcg      672
Arg Asp Gly Lys Glu Asp His Phe His Tyr Glu Gly Gly Ile Lys Ala
        210                 215                 220 ttc gtt gaa tat ctg aac aag aac aaa acg ccg atc cac ccg aat atc      720
Phe Val Glu Tyr Leu Asn Lys Asn Lys Thr Pro Ile His Pro Asn Ile
225                 230                 235                 240 ttc tac ttc tcc act gaa aaa gac ggt att ggc gtc gaa gtg gcg ttg      768
Phe Tyr Phe Ser Thr Glu Lys Asp Gly Ile Gly Val Glu Val Ala Leu
                245                 250                 255
```

```
cag tgg aac gat ggc ttc cag gaa aac atc tac tgc ttt acc aac aac    816
Gln Trp Asn Asp Gly Phe Gln Glu Asn Ile Tyr Cys Phe Thr Asn Asn
            260                 265                 270 att ccg cag cgt gac ggc ggt act cac ctg gca ggc ttc cgt gcg gcg    864
Ile Pro Gln Arg Asp Gly Gly Thr His Leu Ala Gly Phe Arg Ala Ala
        275                 280                 285 atg acc cgt acc ctg aac gcc tac atg gac aaa gaa ggc tac agc aaa    912
Met Thr Arg Thr Leu Asn Ala Tyr Met Asp Lys Glu Gly Tyr Ser Lys
    290                 295                 300 aaa gcc aaa gtc agc gcc acc ggt gac gat gcg cgt gaa ggc ctg att    960
Lys Ala Lys Val Ser Ala Thr Gly Asp Asp Ala Arg Glu Gly Leu Ile
305                 310                 315                 320 gcg gtc gtt tcc gtg aaa gtg ccg gac ccg aaa ttc tcc tcc cag acc   1008
Ala Val Val Ser Val Lys Val Pro Asp Pro Lys Phe Ser Ser Gln Thr
                325                 330                 335 aaa gac aaa ctg gtt tct tct gag gtg aaa tcg gcg gtt gaa cag cag   1056
Lys Asp Lys Leu Val Ser Ser Glu Val Lys Ser Ala Val Glu Gln Gln
            340                 345                 350 atg aac gaa ctg ctg gca gaa tac ctg ctg gaa aac cca acc gac gcg   1104
Met Asn Glu Leu Leu Ala Glu Tyr Leu Leu Glu Asn Pro Thr Asp Ala
        355                 360                 365 aaa atc gtg gtt ggc aaa att atc gat gct gcc cgt gcc cgt gaa gcg   1152
Lys Ile Val Val Gly Lys Ile Ile Asp Ala Ala Arg Ala Arg Glu Ala
    370                 375                 380 gcg cgt cgc gcg cgt gaa atg acc cgc cgt aaa ggt gcg ctc gac tta   1200
Ala Arg Arg Ala Arg Glu Met Thr Arg Arg Lys Gly Ala Leu Asp Leu
385                 390                 395                 400 gcg ggc ctg ccg ggc aaa ctg gca gac tgc cag gaa cgc gat ccg gcg   1248
Ala Gly Leu Pro Gly Lys Leu Ala Asp Cys Gln Glu Arg Asp Pro Ala
                405                 410                 415 ctt tcc gaa ctg tac ctg gtg gaa ggg gac tcc gcg ggc ggc tct gcg   1296
Leu Ser Glu Leu Tyr Leu Val Glu Gly Asp Ser Ala Gly Gly Ser Ala
            420                 425                 430 aag cag ggg cgt aac cgc aag aac cag gcg att ctg ccg ctg aag ggt   1344
Lys Gln Gly Arg Asn Arg Lys Asn Gln Ala Ile Leu Pro Leu Lys Gly
        435                 440                 445 aaa atc ctc aac gtc gag aaa gcg cgc ttc gat aag atg ctc tct tct   1392
Lys Ile Leu Asn Val Glu Lys Ala Arg Phe Asp Lys Met Leu Ser Ser
    450                 455                 460 cag gaa gtg gcg acg ctt atc acc gcg ctt ggc tgt ggt atc ggt cgt   1440
Gln Glu Val Ala Thr Leu Ile Thr Ala Leu Gly Cys Gly Ile Gly Arg
465                 470                 475                 480 gac gag tac aac ccg gac aaa ctg cgt tat cac agc atc atc atc atg   1488
Asp Glu Tyr Asn Pro Asp Lys Leu Arg Tyr His Ser Ile Ile Ile Met
                485                 490                 495 acc gat gcg gac gtc gac ggc tcg cac att cgt acg ctg ctg ttg acc   1536
Thr Asp Ala Asp Val Asp Gly Ser His Ile Arg Thr Leu Leu Leu Thr
            500                 505                 510 ttc ttc tat cgt cag atg ccg gaa atc gtt gaa cgc ggt cac gtc tat   1584
Phe Phe Tyr Arg Gln Met Pro Glu Ile Val Glu Arg Gly His Val Tyr
        515                 520                 525 atc gct cag ccg ccg ctg tac aaa gtg aag aaa ggc aag cag gaa cag   1632
Ile Ala Gln Pro Pro Leu Tyr Lys Val Lys Lys Gly Lys Gln Glu Gln
    530                 535                 540 tac att aaa gac gac gaa gcg atg gat cag tac cag atc tct atc gcg   1680
Tyr Ile Lys Asp Asp Glu Ala Met Asp Gln Tyr Gln Ile Ser Ile Ala
545                 550                 555                 560 ctg gac ggc gca acg ctg cac acc aac gcc agt gca ccg gca ttg gct   1728
Leu Asp Gly Ala Thr Leu His Thr Asn Ala Ser Ala Pro Ala Leu Ala
                565                 570                 575
```

| | | | | | | | | | | | | | | | | |
|---|---|---|---|---|---|---|---|---|---|---|---|---|---|---|---|---|
| ggc | gaa | gcg | tta | gag | aaa | ctg | gta | tct | gag | tac | aac | gcg | acg | cag | aaa | 1776 |
| Gly | Glu | Ala | Leu | Glu | Lys | Leu | Val | Ser | Glu | Tyr | Asn | Ala | Thr | Gln | Lys | |
| | | | 580 | | | | | 585 | | | | | 590 | | | |
| atg | atc | aat | cgt | atg | gag | cgt | cgt | tat | ccg | aaa | gca | atg | ctg | aaa | gag | 1824 |
| Met | Ile | Asn | Arg | Met | Glu | Arg | Arg | Tyr | Pro | Lys | Ala | Met | Leu | Lys | Glu | |
| | | 595 | | | | | 600 | | | | | 605 | | | | |
| ctt | atc | tat | cag | ccg | acg | ttg | acg | gaa | gct | gac | ctt | tct | gat | gag | cag | 1872 |
| Leu | Ile | Tyr | Gln | Pro | Thr | Leu | Thr | Glu | Ala | Asp | Leu | Ser | Asp | Glu | Gln | |
| | 610 | | | | | 615 | | | | | 620 | | | | | |
| acc | gtt | acc | cgc | tgg | gtg | aac | gcg | ctg | gtc | agc | gaa | ctg | aac | gac | aaa | 1920 |
| Thr | Val | Thr | Arg | Trp | Val | Asn | Ala | Leu | Val | Ser | Glu | Leu | Asn | Asp | Lys | |
| 625 | | | | | 630 | | | | | 635 | | | | | 640 | |
| gaa | cag | cac | ggc | agc | cag | tgg | aag | ttt | gat | gtt | cac | acc | aat | gct | gag | 1968 |
| Glu | Gln | His | Gly | Ser | Gln | Trp | Lys | Phe | Asp | Val | His | Thr | Asn | Ala | Glu | |
| | | | | 645 | | | | | 650 | | | | | 655 | | |
| caa | aac | ctg | ttc | gag | ccg | att | gtt | cgc | gtg | cgt | acc | cac | ggt | gtg | gat | 2016 |
| Gln | Asn | Leu | Phe | Glu | Pro | Ile | Val | Arg | Val | Arg | Thr | His | Gly | Val | Asp | |
| | | | 660 | | | | | 665 | | | | | 670 | | | |
| act | gac | tat | ccg | ctg | gat | cac | gag | ttt | atc | acc | ggt | ggc | gaa | tat | cgt | 2064 |
| Thr | Asp | Tyr | Pro | Leu | Asp | His | Glu | Phe | Ile | Thr | Gly | Gly | Glu | Tyr | Arg | |
| | | 675 | | | | | 680 | | | | | 685 | | | | |
| cgt | atc | tgc | acg | ctg | ggt | gag | aaa | ctg | cgt | ggc | ttg | ctg | gaa | gaa | gat | 2112 |
| Arg | Ile | Cys | Thr | Leu | Gly | Glu | Lys | Leu | Arg | Gly | Leu | Leu | Glu | Glu | Asp | |
| | 690 | | | | | 695 | | | | | 700 | | | | | |
| gcg | ttt | atc | gaa | cgt | ggc | gag | cgt | cgt | cag | ccg | gta | gcc | agc | ttc | gag | 2160 |
| Ala | Phe | Ile | Glu | Arg | Gly | Glu | Arg | Arg | Gln | Pro | Val | Ala | Ser | Phe | Glu | |
| 705 | | | | | 710 | | | | | 715 | | | | | 720 | |
| cag | gcg | ctg | gac | tgg | ctg | gtg | aaa | gag | tcc | cgt | cgc | ggc | ctc | tcc | atc | 2208 |
| Gln | Ala | Leu | Asp | Trp | Leu | Val | Lys | Glu | Ser | Arg | Arg | Gly | Leu | Ser | Ile | |
| | | | | 725 | | | | | 730 | | | | | 735 | | |
| cag | cgt | tat | aaa | ggt | ctg | ggc | gag | atg | aac | ccg | gaa | cag | ctg | tgg | gaa | 2256 |
| Gln | Arg | Tyr | Lys | Gly | Leu | Gly | Glu | Met | Asn | Pro | Glu | Gln | Leu | Trp | Glu | |
| | | | 740 | | | | | 745 | | | | | 750 | | | |
| acc | act | atg | gac | ccg | gaa | agt | cgt | cgt | atg | ctg | cgc | gtt | acc | gtt | aaa | 2304 |
| Thr | Thr | Met | Asp | Pro | Glu | Ser | Arg | Arg | Met | Leu | Arg | Val | Thr | Val | Lys | |
| | | 755 | | | | | 760 | | | | | 765 | | | | |
| gat | gcg | att | gct | gcc | gac | cag | ttg | ttc | acc | acg | ctg | atg | ggc | gac | gcc | 2352 |
| Asp | Ala | Ile | Ala | Ala | Asp | Gln | Leu | Phe | Thr | Thr | Leu | Met | Gly | Asp | Ala | |
| | 770 | | | | | 775 | | | | | 780 | | | | | |
| gtt | gaa | ccg | cgc | cgt | gcg | ttt | att | gaa | gag | aac | gcc | ctg | aaa | gcg | gcg | 2400 |
| Val | Glu | Pro | Arg | Arg | Ala | Phe | Ile | Glu | Glu | Asn | Ala | Leu | Lys | Ala | Ala | |
| 785 | | | | | 790 | | | | | 795 | | | | | 800 | |
| aat | atc | gat | att | | | | | | | | | | | | | 2412 |
| Asn | Ile | Asp | Ile | | | | | | | | | | | | | |

<210> SEQ ID NO 2
<211> LENGTH: 804
<212> TYPE: PRT
<213> ORGANISM: Escherichia coli

<400> SEQUENCE: 2

Met Ser Asn Ser Tyr Asp Ser Ser Ser Ile Lys Val Leu Lys Gly Leu
1               5                   10                  15

Asp Ala Val Arg Lys Arg Pro Gly Met Tyr Ile Gly Asp Thr Asp Asp
                20                  25                  30

Gly Thr Gly Leu His His Met Val Phe Glu Val Val Asp Asn Ala Ile
            35                  40                  45

Asp Glu Ala Leu Ala Gly His Cys Lys Glu Ile Ile Val Thr Ile His
        50                  55                  60

```
Ala Asp Asn Ser Val Ser Val Gln Asp Asp Gly Arg Gly Ile Pro Thr
 65                  70                  75                  80

Gly Ile His Pro Glu Glu Gly Val Ser Ala Glu Val Ile Met Thr
                 85                  90                  95

Val Leu His Ala Gly Gly Lys Phe Asp Asp Asn Ser Tyr Lys Val Ser
                100                 105                 110

Gly Gly Leu His Gly Val Gly Val Ser Val Val Asn Ala Leu Ser Gln
                115                 120                 125

Lys Leu Glu Leu Val Ile Gln Arg Glu Gly Lys Ile His Arg Gln Ile
                130                 135                 140

Tyr Glu His Gly Val Pro Gln Ala Pro Leu Ala Val Thr Gly Glu Thr
145                 150                 155                 160

Glu Lys Thr Gly Thr Met Val Arg Phe Trp Pro Ser Leu Glu Thr Phe
                165                 170                 175

Thr Asn Val Thr Glu Phe Glu Tyr Glu Ile Leu Ala Lys Arg Leu Arg
                180                 185                 190

Glu Leu Ser Phe Leu Asn Ser Gly Val Ser Ile Arg Leu Arg Asp Lys
                195                 200                 205

Arg Asp Gly Lys Glu Asp His Phe His Tyr Glu Gly Gly Ile Lys Ala
                210                 215                 220

Phe Val Glu Tyr Leu Asn Lys Asn Lys Thr Pro Ile His Pro Asn Ile
225                 230                 235                 240

Phe Tyr Phe Ser Thr Glu Lys Asp Gly Ile Gly Val Glu Val Ala Leu
                245                 250                 255

Gln Trp Asn Asp Gly Phe Gln Glu Asn Ile Tyr Cys Phe Thr Asn Asn
                260                 265                 270

Ile Pro Gln Arg Asp Gly Gly Thr His Leu Ala Gly Phe Arg Ala Ala
                275                 280                 285

Met Thr Arg Thr Leu Asn Ala Tyr Met Asp Lys Glu Gly Tyr Ser Lys
                290                 295                 300

Lys Ala Lys Val Ser Ala Thr Gly Asp Asp Ala Arg Glu Gly Leu Ile
305                 310                 315                 320

Ala Val Val Ser Val Lys Val Pro Asp Pro Lys Phe Ser Ser Gln Thr
                325                 330                 335

Lys Asp Lys Leu Val Ser Ser Glu Val Lys Ser Ala Val Glu Gln Gln
                340                 345                 350

Met Asn Glu Leu Leu Ala Glu Tyr Leu Leu Glu Asn Pro Thr Asp Ala
                355                 360                 365

Lys Ile Val Val Gly Lys Ile Ile Asp Ala Ala Arg Ala Arg Glu Ala
                370                 375                 380

Ala Arg Arg Ala Arg Glu Met Thr Arg Arg Lys Gly Ala Leu Asp Leu
385                 390                 395                 400

Ala Gly Leu Pro Gly Lys Leu Ala Asp Cys Gln Glu Arg Asp Pro Ala
                405                 410                 415

Leu Ser Glu Leu Tyr Leu Val Glu Gly Asp Ser Ala Gly Gly Ser Ala
                420                 425                 430

Lys Gln Gly Arg Asn Arg Lys Asn Gln Ala Ile Leu Pro Leu Lys Gly
                435                 440                 445

Lys Ile Leu Asn Val Glu Lys Ala Arg Phe Asp Lys Met Leu Ser Ser
                450                 455                 460

Gln Glu Val Ala Thr Leu Ile Thr Ala Leu Gly Cys Gly Ile Gly Arg
465                 470                 475                 480
```

```
Asp Glu Tyr Asn Pro Asp Lys Leu Arg Tyr His Ser Ile Ile Ile Met
                485                 490                 495

Thr Asp Ala Asp Val Asp Gly Ser His Ile Arg Thr Leu Leu Leu Thr
            500                 505                 510

Phe Phe Tyr Arg Gln Met Pro Glu Ile Val Glu Arg Gly His Val Tyr
        515                 520                 525

Ile Ala Gln Pro Pro Leu Tyr Lys Val Lys Lys Gly Lys Gln Glu Gln
    530                 535                 540

Tyr Ile Lys Asp Asp Glu Ala Met Asp Gln Tyr Gln Ile Ser Ile Ala
545                 550                 555                 560

Leu Asp Gly Ala Thr Leu His Thr Asn Ala Ser Pro Ala Leu Ala
                565                 570                 575

Gly Glu Ala Leu Glu Lys Leu Val Ser Glu Tyr Asn Ala Thr Gln Lys
            580                 585                 590

Met Ile Asn Arg Met Glu Arg Arg Tyr Pro Lys Ala Met Leu Lys Glu
        595                 600                 605

Leu Ile Tyr Gln Pro Thr Leu Thr Glu Ala Asp Leu Ser Asp Glu Gln
    610                 615                 620

Thr Val Thr Arg Trp Val Asn Ala Leu Val Ser Glu Leu Asn Asp Lys
625                 630                 635                 640

Glu Gln His Gly Ser Gln Trp Lys Phe Asp Val His Thr Asn Ala Glu
                645                 650                 655

Gln Asn Leu Phe Glu Pro Ile Val Arg Val Arg Thr His Gly Val Asp
            660                 665                 670

Thr Asp Tyr Pro Leu Asp His Glu Phe Ile Thr Gly Glu Tyr Arg
        675                 680                 685

Arg Ile Cys Thr Leu Gly Glu Lys Leu Arg Gly Leu Leu Glu Glu Asp
    690                 695                 700

Ala Phe Ile Glu Arg Gly Glu Arg Arg Gln Pro Val Ala Ser Phe Glu
705                 710                 715                 720

Gln Ala Leu Asp Trp Leu Val Lys Glu Ser Arg Arg Gly Leu Ser Ile
                725                 730                 735

Gln Arg Tyr Lys Gly Leu Gly Glu Met Asn Pro Glu Gln Leu Trp Glu
            740                 745                 750

Thr Thr Met Asp Pro Glu Ser Arg Arg Met Leu Arg Val Thr Val Lys
        755                 760                 765

Asp Ala Ile Ala Ala Asp Gln Leu Phe Thr Thr Leu Met Gly Asp Ala
    770                 775                 780

Val Glu Pro Arg Arg Ala Phe Ile Glu Glu Asn Ala Leu Lys Ala Ala
785                 790                 795                 800

Asn Ile Asp Ile

<210> SEQ ID NO 3
<211> LENGTH: 657
<212> TYPE: DNA
<213> ORGANISM: Escherichia coli
<220> FEATURE:
<221> NAME/KEY: CDS
<222> LOCATION: (1)..(657)

<400> SEQUENCE: 3 tcg aat tct tat gac tcc tcc agt atc aaa gtc ctg aaa ggg ctg gat    48
Ser Asn Ser Tyr Asp Ser Ser Ser Ile Lys Val Leu Lys Gly Leu Asp
 1               5                  10                  15
```

-continued

```
gcg gtg cgt aag cgc ccg ggt atg tat atc ggc gac acg gat gac ggc      96
Ala Val Arg Lys Arg Pro Gly Met Tyr Ile Gly Asp Thr Asp Asp Gly
         20                  25                  30 acc ggt ctg cac cac atg gta ttc gag gtg gta gat aac gct atc gac     144
Thr Gly Leu His His Met Val Phe Glu Val Val Asp Asn Ala Ile Asp
     35                  40                  45 gaa gcg ctc gcg ggt cac tgt aaa gaa att atc gtc acc att cac gcc     192
Glu Ala Leu Ala Gly His Cys Lys Glu Ile Ile Val Thr Ile His Ala
 50                  55                  60 gat aac tct gtc tct gta cag gat gac ggg cgc ggt att ccg acc ggt     240
Asp Asn Ser Val Ser Val Gln Asp Asp Gly Arg Gly Ile Pro Thr Gly
 65                  70                  75                  80 att cac ccg gaa gag ggc gta tcg gcg gcg gaa gtg atc atg acc gtt     288
Ile His Pro Glu Glu Gly Val Ser Ala Ala Glu Val Ile Met Thr Val
                 85                  90                  95 ctg cac gca ggc ggt aaa ttt gac gat aac tcc tat aaa gtg tcc ggc     336
Leu His Ala Gly Gly Lys Phe Asp Asp Asn Ser Tyr Lys Val Ser Gly
            100                 105                 110 ggt ctg cac ggc gtt ggt gtt tcg gta gta aac gcc ctg tcg caa aaa     384
Gly Leu His Gly Val Gly Val Ser Val Val Asn Ala Leu Ser Gln Lys
        115                 120                 125 ctg gag ctg gtt atc cag cgc gag ggt aaa att cac cgt cag atc tac     432
Leu Glu Leu Val Ile Gln Arg Glu Gly Lys Ile His Arg Gln Ile Tyr
    130                 135                 140 gaa cac ggt gta ccg cag gcc ccg ctg gcg gtt acc ggc gag act gaa     480
Glu His Gly Val Pro Gln Ala Pro Leu Ala Val Thr Gly Glu Thr Glu
145                 150                 155                 160 aaa acc ggc acc atg gtg cgt ttc tgg ccc agc ctc gaa acc ttc acc     528
Lys Thr Gly Thr Met Val Arg Phe Trp Pro Ser Leu Glu Thr Phe Thr
                165                 170                 175 aat gtg acc gag ttc gaa tat gaa att ctg gcg aaa cgt ctg cgt gag     576
Asn Val Thr Glu Phe Glu Tyr Glu Ile Leu Ala Lys Arg Leu Arg Glu
            180                 185                 190 ttg tcg ttc ctc aac tcc ggc gtt tcc att cgt ctg cgc gac aag cgc     624
Leu Ser Phe Leu Asn Ser Gly Val Ser Ile Arg Leu Arg Asp Lys Arg
        195                 200                 205 gac ggc aaa gaa gac cac ttc cac tat gaa ggc                         657
Asp Gly Lys Glu Asp His Phe His Tyr Glu Gly
    210                 215
```

<210> SEQ ID NO 4
<211> LENGTH: 219
<212> TYPE: PRT
<213> ORGANISM: Escherichia coli

<400> SEQUENCE: 4

```
Ser Asn Ser Tyr Asp Ser Ser Ile Lys Val Leu Lys Gly Leu Asp
 1               5                  10                  15

Ala Val Arg Lys Arg Pro Gly Met Tyr Ile Gly Asp Thr Asp Asp Gly
             20                  25                  30

Thr Gly Leu His His Met Val Phe Glu Val Val Asp Asn Ala Ile Asp
         35                  40                  45

Glu Ala Leu Ala Gly His Cys Lys Glu Ile Ile Val Thr Ile His Ala
     50                  55                  60

Asp Asn Ser Val Ser Val Gln Asp Asp Gly Arg Gly Ile Pro Thr Gly
 65                  70                  75                  80

Ile His Pro Glu Glu Gly Val Ser Ala Ala Glu Val Ile Met Thr Val
                 85                  90                  95
```

```
Leu His Ala Gly Gly Lys Phe Asp Asp Asn Ser Tyr Lys Val Ser Gly
        100                 105                 110
Gly Leu His Gly Val Gly Val Ser Val Val Asn Ala Leu Ser Gln Lys
            115                 120                 125
Leu Glu Leu Val Ile Gln Arg Glu Gly Lys Ile His Arg Gln Ile Tyr
130                 135                 140
Glu His Gly Val Pro Gln Ala Pro Leu Ala Val Thr Gly Glu Thr Glu
145                 150                 155                 160
Lys Thr Gly Thr Met Val Arg Phe Trp Pro Ser Leu Glu Thr Phe Thr
                165                 170                 175
Asn Val Thr Glu Phe Glu Tyr Glu Ile Leu Ala Lys Arg Leu Arg Glu
            180                 185                 190
Leu Ser Phe Leu Asn Ser Gly Val Ser Ile Arg Leu Arg Asp Lys Arg
        195                 200                 205
Asp Gly Lys Glu Asp His Phe His Tyr Glu Gly
    210                 215
```

<210> SEQ ID NO 5
<211> LENGTH: 711
<212> TYPE: DNA
<213> ORGANISM: Enterobacteria phage lambda
<220> FEATURE:
<221> NAME/KEY: CDS
<222> LOCATION: (1)..(711)

<400> SEQUENCE: 5

```
atg agc aca aaa aag aaa cca tta aca caa gag cag ctt gag gac gca      48
Met Ser Thr Lys Lys Lys Pro Leu Thr Gln Glu Gln Leu Glu Asp Ala
1               5                   10                  15 cgt cgc ctt aaa gca att tat gaa aaa aag aaa aat gaa ctt ggc tta      96
Arg Arg Leu Lys Ala Ile Tyr Glu Lys Lys Lys Asn Glu Leu Gly Leu
            20                  25                  30 tcc cag gaa tct gtc gca gac aag atg ggg atg ggg cag tca ggc gtt     144
Ser Gln Glu Ser Val Ala Asp Lys Met Gly Met Gly Gln Ser Gly Val
        35                  40                  45 ggt gct tta ttt aat ggc atc aat gca tta aat gct tat aac gcc gca     192
Gly Ala Leu Phe Asn Gly Ile Asn Ala Leu Asn Ala Tyr Asn Ala Ala
    50                  55                  60 ttg ctt gca aaa att ctc aaa gtt agc gtt gaa gaa ttt agc cct tca     240
Leu Leu Ala Lys Ile Leu Lys Val Ser Val Glu Glu Phe Ser Pro Ser
65                  70                  75                  80 atc gcc aga gaa atc tac gag atg tat gaa gcg gtt agt atg cag ccg     288
Ile Ala Arg Glu Ile Tyr Glu Met Tyr Glu Ala Val Ser Met Gln Pro
                85                  90                  95 tca ctt aga agt gag tat gag tac cct gtt ttt tct cat gtt cag gca     336
Ser Leu Arg Ser Glu Tyr Glu Tyr Pro Val Phe Ser His Val Gln Ala
            100                 105                 110 ggg atg ttc tca cct gag ctt aga acc ttt acc aaa ggt gat gcg gag     384
Gly Met Phe Ser Pro Glu Leu Arg Thr Phe Thr Lys Gly Asp Ala Glu
        115                 120                 125 aga tgg gta agc aca acc aaa aaa gcc agt gat tct gca ttc tgg ctt     432
Arg Trp Val Ser Thr Thr Lys Lys Ala Ser Asp Ser Ala Phe Trp Leu
    130                 135                 140 gag gtt gaa ggt aat tcc atg acc gca cca aca ggc tcc aag cca agc     480
Glu Val Glu Gly Asn Ser Met Thr Ala Pro Thr Gly Ser Lys Pro Ser
145                 150                 155                 160 ttt cct gac gga atg tta att ctc gtt gac cct gag cag gct gtt gag     528
Phe Pro Asp Gly Met Leu Ile Leu Val Asp Pro Glu Gln Ala Val Glu
                165                 170                 175
```

```
cca ggt gat ttc tgc ata gcc aga ctt ggg ggt gat gag ttt acc ttc     576
Pro Gly Asp Phe Cys Ile Ala Arg Leu Gly Gly Asp Glu Phe Thr Phe
            180                 185                 190 aag aaa ctg atc agg gat agc ggt cag gtg ttt tta caa cca cta aac     624
Lys Lys Leu Ile Arg Asp Ser Gly Gln Val Phe Leu Gln Pro Leu Asn
        195                 200                 205 cca cag tac cca atg atc cca tgc aat gag agt tgt tcc gtt gtg ggg     672
Pro Gln Tyr Pro Met Ile Pro Cys Asn Glu Ser Cys Ser Val Val Gly
    210                 215                 220 aaa gtt atc gct agt cag tgg cct gaa gag acg ttt ggc                 711
Lys Val Ile Ala Ser Gln Trp Pro Glu Glu Thr Phe Gly
225                 230                 235

<210> SEQ ID NO 6
<211> LENGTH: 237
<212> TYPE: PRT
<213> ORGANISM: Enterobacteria phage lambda

<400> SEQUENCE: 6

Met Ser Thr Lys Lys Pro Leu Thr Gln Glu Gln Leu Glu Asp Ala
 1               5                  10                  15

Arg Arg Leu Lys Ala Ile Tyr Glu Lys Lys Asn Glu Leu Gly Leu
            20                  25                  30

Ser Gln Glu Ser Val Ala Asp Lys Met Gly Met Gly Gln Ser Gly Val
        35                  40                  45

Gly Ala Leu Phe Asn Gly Ile Asn Ala Leu Asn Ala Tyr Asn Ala Ala
    50                  55                  60

Leu Leu Ala Lys Ile Leu Lys Val Ser Val Glu Glu Phe Ser Pro Ser
65                  70                  75                  80

Ile Ala Arg Glu Ile Tyr Glu Met Tyr Glu Ala Val Ser Met Gln Pro
                85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Gly Asp Ala Glu
        115                 120                 125

Arg Trp Val Ser Thr Thr Lys Lys Ala Ser Asp Ser Ala Phe Trp Leu
    130                 135                 140

Glu Val Glu Gly Asn Ser Met Thr Ala Pro Thr Gly Ser Lys Pro Ser
145                 150                 155                 160

Phe Pro Asp Gly Met Leu Ile Leu Val Asp Pro Glu Gln Ala Val Glu
                165                 170                 175

Pro Gly Asp Phe Cys Ile Ala Arg Leu Gly Gly Asp Glu Phe Thr Phe
            180                 185                 190

Lys Lys Leu Ile Arg Asp Ser Gly Gln Val Phe Leu Gln Pro Leu Asn
        195                 200                 205

Pro Gln Tyr Pro Met Ile Pro Cys Asn Glu Ser Cys Ser Val Val Gly
    210                 215                 220

Lys Val Ile Ala Ser Gln Trp Pro Glu Glu Thr Phe Gly
225                 230                 235

<210> SEQ ID NO 7
<211> LENGTH: 393
<212> TYPE: DNA
<213> ORGANISM: Enterobacteria phage lambda
<220> FEATURE:
<221> NAME/KEY: CDS
<222> LOCATION: (1)..(393)

<400> SEQUENCE: 7
```

```
atg agc aca aaa aag aaa cca tta aca caa gag cag ctt gag gac gca      48
Met Ser Thr Lys Lys Lys Pro Leu Thr Gln Glu Gln Leu Glu Asp Ala
 1               5                  10                  15 cgt cgc ctt aaa gca att tat gaa aaa aag aaa aat gaa ctt ggc tta      96
Arg Arg Leu Lys Ala Ile Tyr Glu Lys Lys Lys Asn Glu Leu Gly Leu
             20                  25                  30 tcc cag gaa tct gtc gca gac aag atg ggg atg ggg cag tca ggc gtt     144
Ser Gln Glu Ser Val Ala Asp Lys Met Gly Met Gly Gln Ser Gly Val
         35                  40                  45 ggt gct tta ttt aat ggc atc aat gca tta aat gct tat aac gcc gca     192
Gly Ala Leu Phe Asn Gly Ile Asn Ala Leu Asn Ala Tyr Asn Ala Ala
     50                  55                  60 ttg ctt gca aaa att ctc aaa gtt agc gtt gaa gaa ttt agc cct tca     240
Leu Leu Ala Lys Ile Leu Lys Val Ser Val Glu Glu Phe Ser Pro Ser
 65                  70                  75                  80 atc gcc aga gaa atc tac gag atg tat gaa gcg gtt agt atg cag ccg     288
Ile Ala Arg Glu Ile Tyr Glu Met Tyr Glu Ala Val Ser Met Gln Pro
                 85                  90                  95 tca ctt aga agt gag tat gag tac cct gtt ttt tct cat gtt cag gca     336
Ser Leu Arg Ser Glu Tyr Glu Tyr Pro Val Phe Ser His Val Gln Ala
            100                 105                 110 ggg atg ttc tca cct gag ctt aga acc ttt acc aaa ggt gat gcg gag     384
Gly Met Phe Ser Pro Glu Leu Arg Thr Phe Thr Lys Gly Asp Ala Glu
        115                 120                 125 aga tgg gta                                                         393
Arg Trp Val
    130
```

<210> SEQ ID NO 8
<211> LENGTH: 131
<212> TYPE: PRT
<213> ORGANISM: Enterobacteria phage lambda

<400> SEQUENCE: 8

```
Met Ser Thr Lys Lys Lys Pro Leu Thr Gln Glu Gln Leu Glu Asp Ala
 1               5                  10                  15

Arg Arg Leu Lys Ala Ile Tyr Glu Lys Lys Lys Asn Glu Leu Gly Leu
             20                  25                  30

Ser Gln Glu Ser Val Ala Asp Lys Met Gly Met Gly Gln Ser Gly Val
         35                  40                  45

Gly Ala Leu Phe Asn Gly Ile Asn Ala Leu Asn Ala Tyr Asn Ala Ala
     50                  55                  60

Leu Leu Ala Lys Ile Leu Lys Val Ser Val Glu Glu Phe Ser Pro Ser
 65                  70                  75                  80

Ile Ala Arg Glu Ile Tyr Glu Met Tyr Glu Ala Val Ser Met Gln Pro
                 85                  90                  95

Ser Leu Arg Ser Glu Tyr Glu Tyr Pro Val Phe Ser His Val Gln Ala
            100                 105                 110

Gly Met Phe Ser Pro Glu Leu Arg Thr Phe Thr Lys Gly Asp Ala Glu
        115                 120                 125

Arg Trp Val
    130
```

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic -continued

```
oligonucleotide

<400> SEQUENCE: 9
tcgagtttac ctctggcggt gatag                                            25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcgactatca ccgccagagg taaac                                            25
```